US011780862B2

(12) United States Patent
Kanouni et al.

(10) Patent No.: US 11,780,862 B2
(45) Date of Patent: Oct. 10, 2023

(54) INHIBITORS OF MEK KINASE

(71) Applicant: Kinnate Biopharma Inc., San Diego, CA (US)

(72) Inventors: Toufike Kanouni, Rancho Santa Fe, CA (US); Robert S. Kania, Del Mar, CA (US); Jason M. Cox, Rancho Santa Fe, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

(21) Appl. No.: 18/175,074

(22) Filed: Feb. 27, 2023

(65) Prior Publication Data

US 2023/0279033 A1    Sep. 7, 2023

Related U.S. Application Data

(60) Provisional application No. 63/316,607, filed on Mar. 4, 2022.

(51) Int. Cl.
*C07F 9/58*  (2006.01)
*C07F 9/6584*  (2006.01)
*C07F 9/53*  (2006.01)

(52) U.S. Cl.
CPC .............. *C07F 9/58* (2013.01); *C07F 9/5325* (2013.01); *C07F 9/6584* (2013.01)

(58) Field of Classification Search
CPC .................................. C07F 9/58; C07F 9/6584
See application file for complete search history.

(56) References Cited

U.S. PATENT DOCUMENTS

| 5,525,625 A | 6/1996 | Bridges et al. |
| 5,846,514 A | 12/1998 | Foster et al. |
| 6,334,997 B1 | 1/2002 | Foster et al. |
| 6,972,298 B2 | 12/2005 | Baragi et al. |

FOREIGN PATENT DOCUMENTS

| CN | 102649773 A | 8/2012 |
| CN | 103570594 A | 2/2014 |
| WO | WO-9843960 A1 | 10/1998 |
| WO | WO-9901421 A1 | 1/1999 |
| WO | WO-9901426 A1 | 1/1999 |
| WO | WO-0041505 A2 | 7/2000 |
| WO | WO-0041994 A1 | 7/2000 |
| WO | WO-0042002 A1 | 7/2000 |
| WO | WO-0042003 A1 | 7/2000 |
| WO | WO-0042022 A1 | 7/2000 |
| WO | WO-0042029 A1 | 7/2000 |
| WO | WO-0068201 A1 | 11/2000 |
| WO | WO-0168619 A1 | 9/2001 |
| WO | WO-0206213 A2 | 1/2002 |
| WO | WO-03062191 A1 | 7/2003 |
| WO | WO-03077855 A2 | 9/2003 |
| WO | WO-03077914 A1 | 9/2003 |
| WO | WO-2004005284 A1 | 1/2004 |
| WO | WO-2004056789 A1 | 7/2004 |
| WO | WO-2005028426 A1 | 3/2005 |
| WO | WO-2006011466 A1 | 2/2006 |
| WO | WO-2006045514 A1 | 5/2006 |
| WO | WO-2007044515 A1 | 4/2007 |
| WO | WO-2007123939 A2 | 11/2007 |
| WO | WO-2009129938 A1 | 10/2009 |
| WO | WO-2010017051 A1 | 2/2010 |
| WO | WO-2012055953 A1 | 5/2012 |
| WO | WO-2020088390 A1 | 5/2020 |
| WO | WO-2020106303 A1 | 5/2020 |

OTHER PUBLICATIONS

Chemical Structure Search dated Apr. 4, 2023.
PCT/US2023/063338 International Search Report and Written Opinion dated Apr. 26, 2023.
Berge et al. Pharmaceutical Salts. Journal of Pharmaceutical Sciences 66(1):1-19 (Jan. 1977).
Dean. Recent Advances in the Synthesis and Applications of Radiolabeled Compounds for Drug Discovery and Development. In: Curr. Pharm. Des., 6(10):110 (2000) (Preface only).
Evans. Synthesis of radiolabeled compounds. J Radioanal Chem 64(1-2):9-32 (1981).
Gampa et al. Brain Distribution of a Novel MEK Inhibitor E6201: Implications in the Treatment of Melanoma Brain Metastases. Drug Metab Dispos 46(5):658-666 (2018).
Han et al. MEK inhibitors for the treatment of non-small cell lung cancer. J Hematol Oncol. 14(1):1 (2021).
Kabalka et al. The Synthesis of Radiolabeled Compounds via Organometallic Intermediates. Tetrahedron 45(21):6601-6621 (1989).
Subbiah et al. Clinical Development of BRAF plus MEK Inhibitor Combinations. Trends in Cancer 6(9):797-810 (2020).

*Primary Examiner* — Laura L Stockton
(74) *Attorney, Agent, or Firm* — WILSON SONSINI GOODRICH & ROSATI

(57) ABSTRACT

Provided herein are inhibitors of MEK kinase, pharmaceutical compositions comprising said inhibitory compounds, and methods for using said MEK kinase inhibitory compounds for the treatment of disease.

27 Claims, No Drawings

INHIBITORS OF MEK KINASE

CROSS-REFERENCE TO RELATED APPLICATION

This application claims the benefit of U.S. Patent Application No. 63/316,607, filed on Mar. 4, 2022, which is hereby incorporated by reference in its entirety.

BACKGROUND

Activation of MEK initiates the mitogen-activated protein kinase (MAPK) pathway, which is a key cell signaling pathway in regulating proliferation, cellular growth, and survival. Given that dysregulation of MAPK signaling has been demonstrated to be a key driver of many cancers, therapies that target MEK kinase activity are desired for use in the treatment of cancer and other disorders characterized by aberrant MEK pathway signaling.

BRIEF SUMMARY OF THE INVENTION

Provided herein are inhibitors of MEK kinase, pharmaceutical compositions comprising said inhibitory compounds, and methods for using said inhibitory compounds for the treatment of disease.

One embodiment provides a compound, or pharmaceutically acceptable salt or solvate thereof, having the structure of Formula (I):

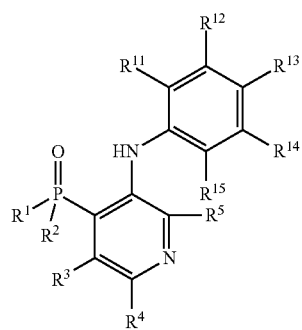

wherein,
- $R^1$ is optionally substituted alkyl;
- $R^2$ is optionally substituted alkyl; optionally, $R^1$ and $R^2$ join with a carbon-carbon bond to form a phosphorous-containing ring;
- $R^3$ is selected from hydrogen, halo, optionally substituted alkyl, optionally substituted cycloalkyl, or optionally substituted alkoxy;
- $R^4$ is selected from hydrogen, halo, optionally substituted alkyl, optionally substituted cycloalkyl, or optionally substituted alkoxy;
- $R^5$ is selected from hydrogen, halo, optionally substituted alkyl, optionally substituted cycloalkyl, or optionally substituted alkoxy; and
- $R^{11}$, $R^{12}$, $R^{13}$, $R^{14}$, and $R^{15}$ are independently selected from hydrogen, halo, optionally substituted alkynyl, optionally substituted alkyl, optionally substituted cycloalkyl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$NR^a$ (where t is 1 or 2), —S(O)$_t$$OR^a$ (where t is 1 or 2), —S(O)$_t$$NR^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$NR^a$ (where t is 1 or 2), —S(O)$_t$$OR^a$ (where t is 1 or 2), —S(O)$_t$$NR^a$ (where t is 1 or 2) and —S(O)$_t$N($R^a$)$_2$ (where t is 1 or 2) where each R is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$NR^a$ (where t is 1 or 2), —S(O)$_t$$OR^a$ (where t is 1 or 2), —S(O)$_t$$NR^a$ (where t is 1 or 2) and —S(O)$_t$N($R^a$)$_2$ (where t is 1 or 2) where each R is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyan, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$NR$^a$ (where t is 1 or 2), —S(O)$_t$OR$^a$ (where t is 1 or 2), —S(O)$_t$NR$^a$ (where t is 1 or 2) and —S(O)$_t$N(R$^a$)$_2$ (where t is 1 or 2) where each R is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$NR$^a$ (where t is 1 or 2), —S(O)$_t$OR$^a$ (where t is 1 or 2), —S(O)$_t$NR$^a$ (where t is 1 or 2) and —S(O)$_t$N(R$^a$)$_2$ (where t is 1 or 2) where each R is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms.

The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$NR$^a$ (where t is 1 or 2), —S(O)$_t$OR$^a$ (where t is 1 or 2), —S(O)$_t$NR$^a$ (where t is 1 or 2) and —S(O)$_t$N(R$^a$)$_2$ (where t is 1 or 2) where each R is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory.

The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C (O)OR$^a$, —R$^b$—N(R$^a$)C(O)R$^a$, —R$^b$—N(R$^a$)S(O)$_t$R$^a$ (where t is 1 or 2), —R$^b$—S(OR$^a$ (where t is 1 or 2), —R$^b$—S(O)OR$^a$ (where t is 1 or 2) and —R$^b$—S(O)$_t$N(R$^a$)$_2$ (where t is 1 or 2), where each R is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, nor- bornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$NR$^a$ (where t is 1 or 2), —R$^b$—S(O)$_t$NR$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tNR^a$ (where t is 1 or 2), $-R^b-S(O)_tNR^a$ (where t is 1 or 2), $-R^b-S(O)_tOR^a$ (where t is 1 or 2) and $-R^b-S(O)N(R^a)_2$ (where t is 1 or 2), where each R is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $-O-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)NR$^a$ (where t is 1 or 2), —R$^b$—S(O)OR$^a$ (where t is 1 or 2) and —R$^b$—S(O)$_t$N(R$^a$)$_2$ (where t is 1 or 2), where each R is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the R$^a$, R$^b$, or R$^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

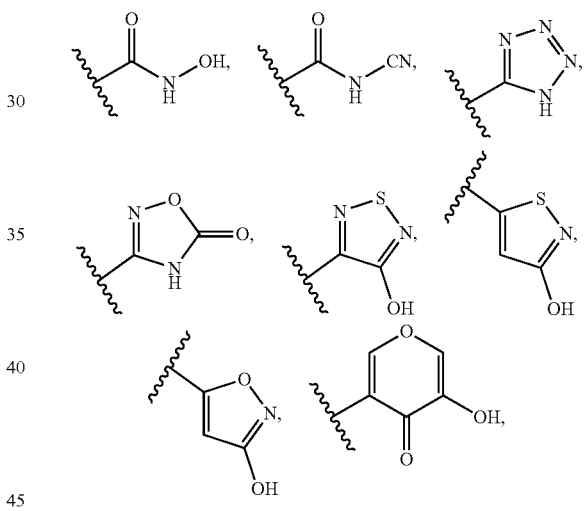

and the like.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

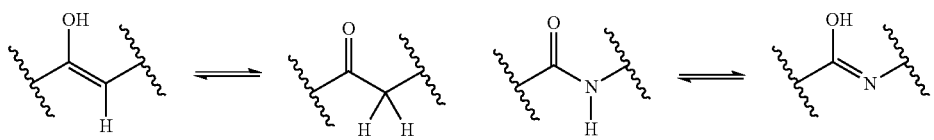

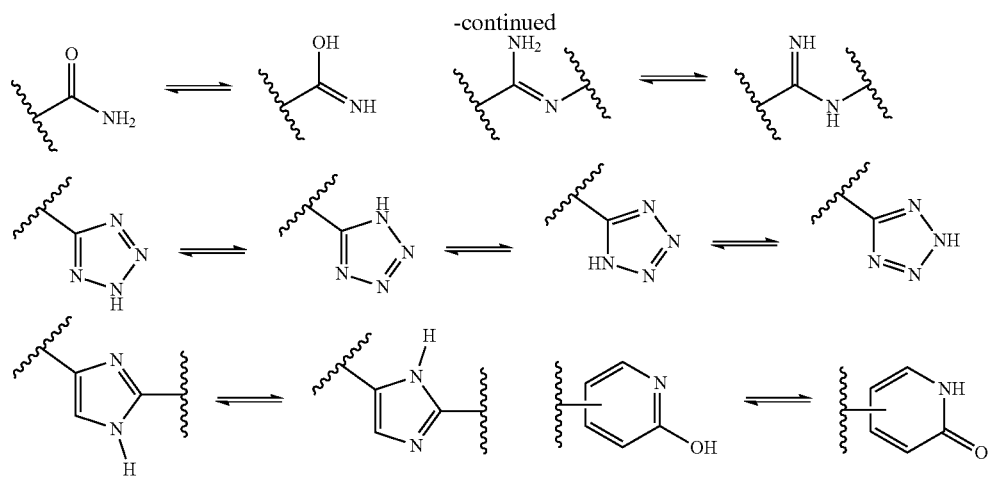

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

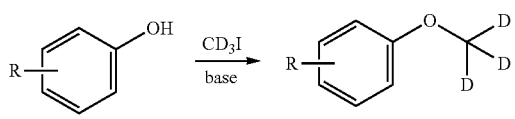

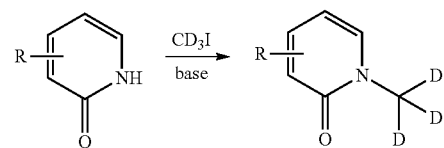

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

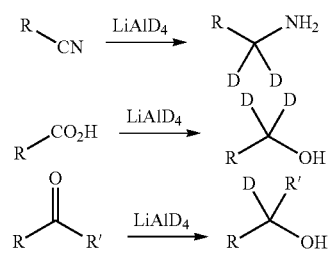

Deuterium gas and palladium catalyst are employed to reduce unsaturated carbon-carbon linkages and to perform a reductive substitution of aryl carbon-halogen bonds as illustrated, by way of example only, in the reaction schemes below.

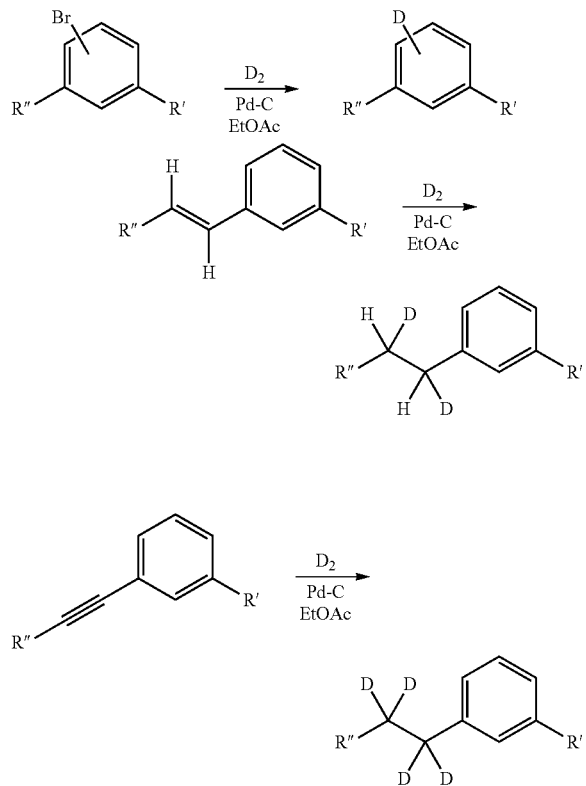

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the MEK kinase inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

MEK Kinase

Phosphorylation of mitogen-activated protein kinase (MAPK) occurs through the action of MEK. MAPK is localized to the cytoplasm of the cell through its specific association of the N-terminal 1-32 residues of MEK in unstimulated cells. To date, there are 7 MEK enzymes that have been identified, and these enzymes selective phosphorylate serin/threonine and tyrosine residues within the activation loop of their specific mitogen-activated protein kinase (MAPK) substrates. MEK family of genes consists of seven genes with MEK1 and MEK2 being the more significant genes. MEK1 exists in human chromosome 15q22.31 and is encoded by the gene MAP2KL. MEK2 exists in human chromosome 9q13.3 and is encoded by the geneMAP2K2.

MEK proteins have a molecular weight range between about 43 and 50 kDa. MEKs can have amino- and carboxy-terminal domains which are more diverse between the different MEK proteins but share extensive homology with the kinase domain. The MEK1 and MEK2 proteins are closely related and have three important domains: (1) a core protein kinase domain (that contains ATP binding site and catalytic apparatus); (2) an N-terminal domain (which contains the inhibitory/allosteric segment, nuclear export sequence, and docking site (D-domain) that aids in binding ERK substrates), and (3) a shorter C-terminal region (which contains the domain for versatile docking (DVD), serving as a determinant binding site for upstream components of the Ras/Raf/MEK/ERK signaling cascade).

MEK3 and MEK6 are similar functionally to MEK1 and MEK2, and encoded by MAP2K3 and MAP2K6 genes, respectively, located on chromosome 17q. MEK3 has a 347 amino acid residues and MEK6 has 334 amino acid residues. While MEK6 differs from MEK3 in terms of the C- and N-terminal regions, the serine/threonine and tyrosine catalytic sites and ATP binding sites are conserved. MEK3 and MEK6 signaling pathways can be activated by growth factor stimulation through RTK, G-protein coupled receptors, intracellular receptors, and toll-like receptors. The cascade can be activated in response to various stimuli include, but not limited to tumor necrosis factor, interleukine-1, cytokines, UV irradiation, physical and chemical stress, and hormones. MEK3 and MEK6 can be activated by MPAK kinase kinases (MAPKKK), which in turn allows MEK3 and MEK to activate p38 MAPK. There are four isoforms of p38 MAP kinase ($\alpha$, $\beta$, $\gamma$ and $\delta$). MEK6 can active all four isoforms, whereas MEK3 can only active the p38$\alpha$ and p38$\beta$ isoforms. The MEK3 and MEK6 with p38 MAPK cascade can promote p53-dependent growth arrest to arrest the cell cycle.

MEK4 and MEK7 are part of the stress-activated protein kinase (SAPK) signaling cascade. MEK4 is encoded by MAP2K4 located on chromosome 17p11.2, and MEK7 is encoded by MAP2K7 located on chromosome 19p13.3. MEK4 and MEK7 are homologous to the other MEK inhibitors through the kinase domains, but differ in their N- and C-terminal subunits. After activation by upstream kinases, such as MAPKKK, Tpl-2, DLK, TAO1, TAO2, TAK1, ASK1, and ASK2, the threonine residues in the activation segment of MEK4 and MEK7, or MEK4 only is phosphorylated. MEK4 and MEK7 can work synergistically to activate JNK protein kinases such as JK1, JNK2, and JNK3. Further, the MEK4 and MEK7 with JNK signaling pathway can act as a key tumor suppression pathway. MEK4 and MEK7 along with substrate JNK can promote apoptosis by phosphorylating and inactivating anti-apoptoic proteins such as, but not including to Bcl2, Bcl-XL, and Mcl-1. MEK4 activity has been shown for normal hepatogensis, B and T-cell lymphopoiesis, and erythropoiesis. MEK4 has also been shown to be down-regulated in 75% of cases of ovarian cancer. There is also hypothesized that loss of MEK4-p38MAPK signaling cascade may be relevant to tumorigenesis.

MEK5 shares about a 40% identify with the other MEK protein kinases, and has a 448 amino acid sequence. MEK5 can be activated by hyperosmotic conditions, oxidative stress, and growth factors. The downstream target of MEK5 is ERK5, which is also known as big MAP kinase 1 (BMK1) since it is twice the size of other MAPKs. The PB1 domain of MEK5 mediates the MEK5 interaction with MEKK2, MEKK3, or ERK5. MEK5-ERK5 signaling can enhance progression through the cell cycle. Overexpression of MEK5 has been associated with cancers of the colon, prostate, breast, lymphoma, and malignant mesothelioma.

MEK Activation and Intracellular Signaling Pathways

Activation of MEK initiates the mitogen-activated protein kinase (MAPK) pathway, which is a key cell signaling pathway in regulating proliferation, cellular growth, and survival. MEK transmits mitogenic signals from outside of the cell to the nucleus through the signaling pathway. MEK1 and MEK2 participate in the in Ras/Raf/MEK/ERK signal transduction cascade, and are activated by ligands binding to receptor tyrosine kinases (RTK), which can lead to dimerization of the receptors and autophosphorylation of specific tyrosine residues in its C-terminal region. The activated receptors can then recruit and phosphorylate adaptor proteins Grb2 and SOS, which interact with GTPase Ras to activate it. H-Ras, K-Ras, and N-Ras function as molecular switches when inactive Ras-GDP is converted to active Ras-GTP. In the activated GTP-bound form, Ras activate Ras kinases (A-Raf, B-Raf, and C-Raf/RaF-1) which in turn activates MEK1 and MEK2 leading to the activation of ERK1 and ERK2.

Activated ERKs can translocate into the nucleus to initiate cellular responses such as apoptosis, angiogenesis, motility, cell proliferation, survival, differentiation, and stress response. The Raf/MEK/ERP MAP kinase pathway promotes cell survival by blocking NF-kB, which will lead to increased transcription of anti-apoptotic and pro-survival genes such as Bcl-2 and Mcl-1. The Ras/Raf/MEK/ERK signaling pathway is activated by several different mechanisms in human cancers. For example, increased ERK1 and ERK2 signaling is often due to direct mutational activity or amplification of genes encoding key components of the Ras/Raf/MEK/ERK pathway. In particular, studies have found that B-Raf is mutated in about 20% of all cancers and more than 60% of melanomas. ERK 1 and ERK2 can also be activated by MEKs in solid tumors including, but not limited to, melanoma, colon, and lung carcinomas.

In tumor cells, specific growth factors combine with transmembrane receptors on the cell surface, leading to increase in RAS activation, and once RAS is activated, the plasma membrane of the cell secretes and activates the downstream molecule RAF kinase. Activation of RAF kinase stimulates a series of protein kinases which form the RAS/RAF/MEK ERK signaling pathway. Further, BRAF and KRAS are two key oncogenes in the MEK signaling pathway, as well as the RAS/RAF/MAPK signaling pathways. Mutations in both KRAS and BRAF genes lead to proliferation, differentiation, and apoptosis of tumor cells by activating the MEK/RAS/RAF/ERK signaling pathway. Both KRAS and BRAF gene mutations have also been identified in non-small cell lung cancer (NSCLC). MEK inhibitors combined with chemotherapy treatment, BRAF inhibitors, immune checkpoint inhibitors, or epidermal growth factor receptor-tyrosine kinase inhibitors have shown improving clinical efficacy and causing delay in the occurrence of drug resistance (Han, J. et al. *J Hematol Oncol* 14; 1, 2021).

The BRAF gene is an important gene in the MAPK pathway, and associated with multiple tumor types, including, but not limited to melanoma, non-small cell lung cancer (NSCLC), and anaplastic thyroid cancer (ATC). BRAF inhibitors have shown efficacy in several cancers. Combination therapy targeting BRAF and MEK have been studied and demonstrated synergistic benefits. The combination blockade of BRAF and MEK are able to delay, or prevent resistance, in patients who develop resistance when BRAF inhibitors are administered as a single agent. BRAF and MEK inhibitor combinations have been approved by the FDA for use in cancer types including, but not limited to, BRAF mutations in melanoma, NSCLC, and ATC (Subbiah, V. et al. *Trends in Cancer*, Vol. 6, No. 9 2020). Further, patents treated with a combination of BRAF and MEK inhibitors have shown overall survival for metastatic melanoma.

MEK Inhibitors

Several agents have been developed to target MEK, including small molecule inhibitors. Most small molecular inhibitors of MEK target the MEK1 and/or MEK2 enzyme. MEK inhibitors include, but are not limited to trametinib, GSK1120212, JTP 74057, pimasertib, selumetinib, PD-0325901, Refametinib, RDEA119, BAY 869766, TAK733, MEK162 (ARRY 438162), RO5126766, WX-554, RO4987655, CH4987655, GDC-0973, AZD8330, ARRY-424704, ARRY-704, and E6201. Small molecule inhibitors currently FDA-approved or undergoing clinical evaluations include TAK-733, binimetinib, cobimetrinib, trametinib, and selumetinib. Other MEK inhibitors include mirdametinib and pimasertib, along with the compounds disclosed in WO2006/045514. Other compounds suitable as MEK inhibitors are also disclosed in U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077855; WO03/077914; WO2004/005284; and WO2004/056789.

MEK inhibitors can be divided into two major classes, ATP non-competitive and ATP competitive inhibitors. Most MEK inhibitors are ATP non-competitive, and bind to an allosteric site adjacent to the ATP site. This allows for high specificity of non-competitive MEK inhibitors.

Trametinib is an allosteric ATP non-competitive inhibitor with potent activity against MEK1 and MEK2 kinases. Trametinib can include cell-cycle arrest by inhibition of p-ERK1 and p-ERK2. Pimasertib is a selective allosteric ATP non-competitive inhibitor of MEK1 and MEK2. Pimasertib can inhibit tumor growth and regression. Selumetinib is also an ATP non-competitive inhibitor which is highly selective for MEK1 and MEK2. Studies have shown that its antitumor activity correlated with decreasing phosphorylation of ERK1 and ERK2. Refametinib is a cyclopropane-1-sulfonamide derivative which exhibits selective allosteric inhibition of MEK1 and MEK2. Rafametinib shows potent activity against xenographs of human melanoma, colon carcinoma, pancreatic cancer, and skin carcinoma in tumor models.

PD-0325901 is a specific and potent synthetic analog of CI-1040, another MEK inhibitor. PD-0325901 also inhibits phosphorylation of ERK1 and ERK2 in melanoma and papillary thyroid cancer cell lines with B-RAF mutation. MEK162 is an inhibitor which targets MEK1 and MEK2. Studies have examined MEK162 in patients with N-Ras and B-Raf mutated advanced melanoma. RO5126766 is a very potent dual MEK/RAF inhibitor, and selectively binds to MEK1 and MEK2 to form a stable complex. The primary mechanism was shown to be through cell cycle arrest. RO4987655 is a highly selective small molecule MEK inhibitor. The compound is a 3-oxo-oxazinane ring structure which confers metabolic stability, and has antitumor efficacy. GDC-0973 is a derivative of methanone, and is a potent small molecule inhibitor of MEK1. GDC-0973 has antineoplastic activity in BRAF and KRAS mutant cancer cell lines. AZD8330 is a newer inhibitor of MEK1 and MEK2 which has been studied in patients with advanced solid tumors.

E6201 is an ATP competitive MEK inhibitor, and exhibits potent activity against melanoma cells. Since melanoma has a high probability to metastasize to the CNS, E6201 may be useful for permeating an intact blood-brain barrier (BBB) (Gampa, G. et al. *Drug Metab Dispos.*, 46(5): 658-666, 2018). E6201 may be beneficial for treating melanoma as a single agent or in combination with a BRAF inhibitor. Further, E6201 may be able to penetrate the BBB to achieve therapeutically active levels.

Despite the increased knowledge of cellular signaling pathways and limited success in translating this knowledge to medicines, there is a large unmet medical need for therapies operating via selective MEK inhibition.

MEK Kinase Inhibitory Compounds

In one aspect, provided herein is a MEK kinase inhibitory compound.

One embodiment provides a compound, or pharmaceutically acceptable salt or solvate thereof, having the structure of Formula (I):

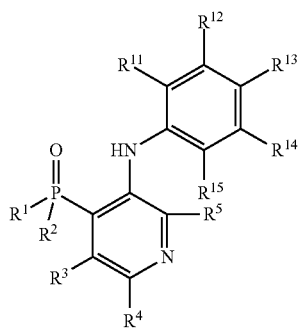

wherein, $R^1$ is optionally substituted alkyl;

$R^2$ is optionally substituted alkyl; optionally, $R^1$ and $R^2$ join with a carbon-carbon bond to form a phosphorous-containing ring;

$R^3$ is selected from hydrogen, halo, optionally substituted alkyl, optionally substituted cycloalkyl, or optionally substituted alkoxy;

$R^4$ is selected from hydrogen, halo, optionally substituted alkyl, optionally substituted cycloalkyl, or optionally substituted alkoxy;

$R^5$ is selected from hydrogen, halo, optionally substituted alkyl, optionally substituted cycloalkyl, or optionally substituted alkoxy; and $R^{11}$, $R^{12}$, $R^{13}$, $R^{14}$, and $R^{15}$ are independently selected from hydrogen, halo, optionally substituted alkynyl, optionally substituted alkyl, optionally substituted cycloalkyl.

Provided herein is the compound of Formula (I), or pharmaceutically acceptable salt or solvate thereof, wherein $R^1$ is optionally substituted C1-C3 alkyl. Provided herein is the compound of Formula (I), or pharmaceutically acceptable salt or solvate thereof, wherein $R^2$ is optionally substituted C1-C3 alkyl. Provided herein is the compound of Formula (I), or pharmaceutically acceptable salt or solvate thereof, wherein $R^1$ is $CH_3$. Provided herein is the compound of Formula (I), or pharmaceutically acceptable salt or solvate thereof, wherein $R^2$ is $CH_3$.

Provided herein is the compound of Formula (I), or pharmaceutically acceptable salt or solvate thereof, wherein $R^1$ is optionally substituted C1-C3 alkyl, $R^2$ is optionally substituted C1-C3 alkyl, and $R^1$ and $R^2$ join with a carbon-carbon bond to form a phosphorous-containing ring. In one embodiment is the compound, or pharmaceutically acceptable salt or solvate thereof, wherein phosphorous-containing ring is a 5-membered ring.

Provided herein is the compound of Formula (I), or pharmaceutically acceptable salt or solvate thereof, wherein $R^3$ is hydrogen. Provided herein is the compound of Formula (I), or pharmaceutically acceptable salt or solvate thereof, wherein $R^3$ is halo. Provided herein is the compound of Formula (I), or pharmaceutically acceptable salt or solvate thereof, wherein $R^3$ is optionally substituted C1-C3 alkyl.

Provided herein is the compound of Formula (I), or pharmaceutically acceptable salt or solvate thereof, wherein $R^4$ is hydrogen. Provided herein is the compound of Formula (I), or pharmaceutically acceptable salt or solvate thereof, wherein $R^4$ is halo. Provided herein is the compound of Formula (I), or pharmaceutically acceptable salt or solvate thereof, wherein $R^4$ is optionally substituted C1-C3 alkyl. Provided herein is the compound of Formula (I), or pharmaceutically acceptable salt or solvate thereof, wherein $R^4$ is optionally substituted C1-C3 alkoxy.

Provided herein is the compound of Formula (I), or pharmaceutically acceptable salt or solvate thereof, wherein $R^5$ is hydrogen. Provided herein is the compound of Formula (I), or pharmaceutically acceptable salt or solvate thereof, wherein $R^5$ is halo. Provided herein is the compound of Formula (I), or pharmaceutically acceptable salt or solvate thereof, wherein $R^5$ is optionally substituted C1-C3 alkyl. Provided herein is the compound of Formula (I), or pharmaceutically acceptable salt or solvate thereof, wherein $R^5$ is optionally substituted C1-C3 alkoxy.

Provided herein is the compound of Formula (I), or pharmaceutically acceptable salt or solvate thereof, wherein $R^{11}$ is fluoro. Provided herein is the compound of Formula (I), or pharmaceutically acceptable salt or solvate thereof, wherein $R^{11}$ is hydrogen.

Provided herein is the compound of Formula (I), or pharmaceutically acceptable salt or solvate thereof, wherein $R^{12}$ is hydrogen or fluoro. Provided herein is the compound of Formula (I), or pharmaceutically acceptable salt or solvate thereof, wherein $R^{12}$ is fluoro. Provided herein is the compound of Formula (I), or pharmaceutically acceptable salt or solvate thereof, wherein $R^{12}$ is hydrogen.

Provided herein is the compound of Formula (I), or pharmaceutically acceptable salt or solvate thereof, wherein $R^{13}$ is selected from iodo, bromo, optionally substituted C2-C3 alkynyl, optionally substituted C1-C3 alkyl, optionally substituted C3-C4 cycloalkyl. Provided herein is the compound of Formula (I), or pharmaceutically acceptable salt or solvate thereof, wherein $R^{13}$ is iodo. Provided herein is the compound of Formula (I), or pharmaceutically acceptable salt or solvate thereof, wherein $R^{13}$ is optionally substituted C1 alkyl. Provided herein is the compound of Formula (I), or pharmaceutically acceptable salt or solvate thereof, wherein $R^{13}$ is —$CF_3$. Provided herein is the compound of Formula (I), or pharmaceutically acceptable salt or solvate thereof, wherein $R^3$ is bromo. Provided herein is the compound of Formula (I), or pharmaceutically acceptable salt or solvate thereof, wherein $R^{13}$ is optionally substituted cyclopropyl.

Provided herein is the compound of Formula (I), or pharmaceutically acceptable salt or solvate thereof, wherein $R^{14}$ and $R^{15}$ are hydrogen.

One embodiment provides an MEK kinase inhibitory compound, or a pharmaceutically acceptable salt or solvate thereof, having a structure presented in Table 1.

TABLE 1

| Synthetic Chemistry Example | Compound Structure | Compound Name |
|---|---|---|
| 1 | 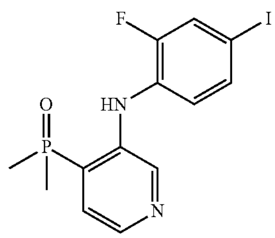 [SMILES: CP(C)(=O)c1ccncc1Nc1ccc(I)cc1F] | 4-(Dimethylphosphoryl)-N-(2-fluoro-4-iodophenyl)pyridin-3-amine |
| 2 | 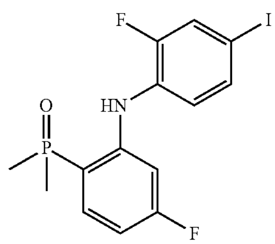 | 2-(Dimethylphosphoryl)-5-fluoro-N-(2-fluoro-4-iodophenyl)aniline |
| 3 | 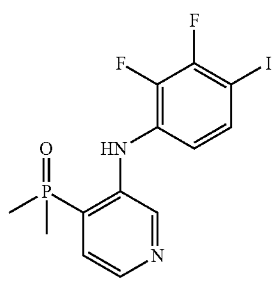 [SMILES: CP(C)(=O)c1ccncc1Nc1ccc(I)c(F)c1F] | N-(2,3-Difluoro-4-iodophenyl)-4-(dimethylphosphoryl)pyridin-3-amine |
| 4 | 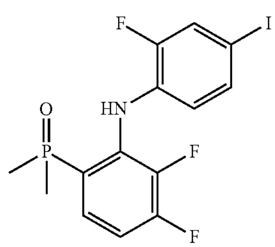 [SMILES: CP(C)(=O)c1ccc(F)c(F)c1Nc1ccc(I)cc1F] | 6-(Dimethylphosphoryl)-2,3-difluoro-N-(2-fluoro-4-iodophenyl)aniline |
| 5 | 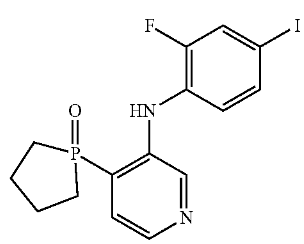 [SMILES: O=P1(c2ccncc2Nc2ccc(I)cc2F)CCCC1] | 1-(3-((2-Fluoro-4-iodophenyl)amino)pyridin-4-yl)phospholane 1-oxide |
| 6 | 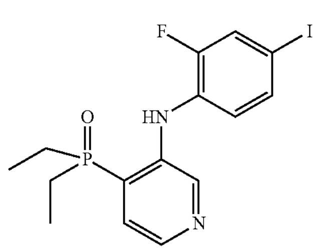 [SMILES: CCP(=O)(CC)c1ccncc1Nc1ccc(I)cc1F] | 4-(Diethylphosphoryl)-N-(2-fluoro-4-iodophenyl)pyridin-3-amine |

TABLE 1-continued

| Synthetic Chemistry Example | Compound Structure | Compound Name |
|---|---|---|
| 7 | 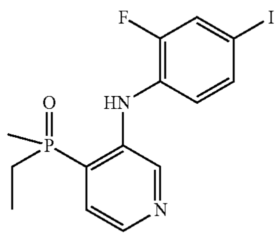 [SMILES: CCP(C)(=O)c1ccncc1Nc1ccc(I)cc1F] | 4-[Ethyl(methyl)phosphoryl]-N-(2-fluoro-4-iodophenyl)pyridin-3-amine |
| 8 | (assumed) | (R)-4-[Ethyl(methyl)phosphoryl]-N-(2-fluoro-4-iodophenyl)pyridin-3-amine |
| 9 | (assumed) | (S)-4-[ethyl(methyl)phosphoryl]-N-(2-fluoro-4-iodophenyl)pyridin-3-amine |
| 10 | 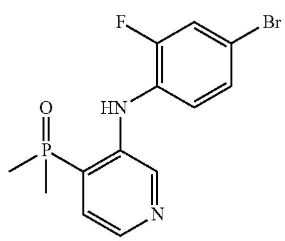 [SMILES: CP(C)(=O)c1ccncc1Nc1ccc(Br)cc1F] | N-(4-Bromo-2-fluorophenyl)-4-(dimethylphosphoryl)pyridin-3-amine |
| 11 | 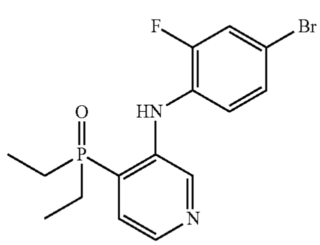 [SMILES: CCP(=O)(CC)c1ccncc1Nc1ccc(Br)cc1F] | N-(4-bromo-2-fluorophenyl)-4-(diethylphosphoryl)pyridin-3-amine |
| 12 | 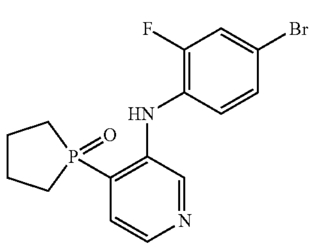 [SMILES: O=P1(c2ccncc2Nc2ccc(Br)cc2F)CCCC1] | 1-(3-((4-Bromo-2-fluorophenyl)amino)pyridin-4-yl)phospholane 1-oxide |

TABLE 1-continued

| Synthetic Chemistry Example | Compound Structure | Compound Name |
|---|---|---|
| 13 | 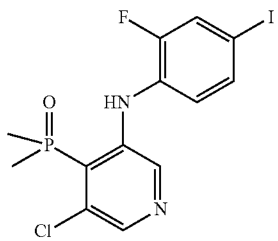 [SMILES: CP(C)(=O)c1c(Cl)cncc1Nc1ccc(I)cc1F] | 5-Chloro-4-(dimethylphosphoryl)-N-(2-fluoro-4-iodophenyl)pyridin-3-amine |
| 14 | 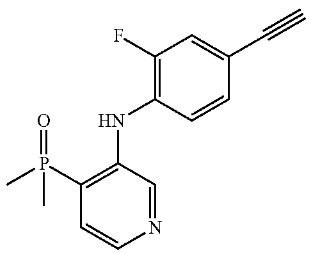 [SMILES: C#Cc1ccc(Nc2cnccc2P(C)(C)=O)c(F)c1] | (3-((4-Ethynyl-2-fluorophenyl)amino)pyridin-4-yl)dimethylphosphine oxide |
| 15 | 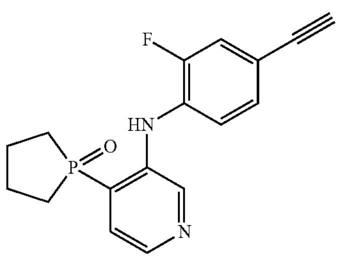 [SMILES: C#Cc1ccc(Nc2cnccc2P2(=O)CCCC2)c(F)c1] | 1-(3-((4-Ethynyl-2-fluorophenyl)amino)pyridin-4-yl)phospholane 1-oxide |
| 16 and 17 | | N-(4-Bromo-2-fluorophenyl)-4-[(R)-ethyl(methyl)phosphoryl]pyridin-3-amine and N-(4-Bromo-2-fluorophenyl)-4-[(S)-ethyl(methyl)phosphoryl]pyridin-3-amine |
| 18 | 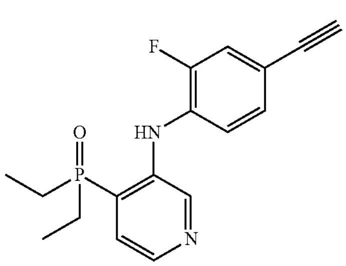 [SMILES: C#Cc1ccc(Nc2cnccc2P(=O)(CC)CC)c(F)c1] | 4-(Diethylphosphoryl)-N-(4-ethynyl-2-fluorophenyl)pyridin-3-amine |

TABLE 1-continued

| Synthetic Chemistry Example | Compound Structure | Compound Name |
|---|---|---|
| 19 and 20 | | 4-[(R)-Ethyl(methyl)phosphoryl]-N-(4-ethynyl-2-fluorophenyl)pyridin-3-amine and 4-[(S)-Ethyl(methyl)phosphoryl]-N-(4-ethynyl-2-fluorophenyl)pyridin-3-amine |
| 21 | 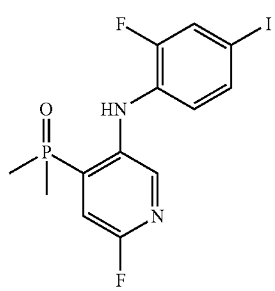 [SMILES: CP(C)(=O)c1cc(F)ncc1Nc1ccc(I)cc1F] | (2-Fluoro-5-((2-fluoro-4-iodophenyl)amino)pyridin-4-yl)dimethylphosphine oxide |
| 22 | 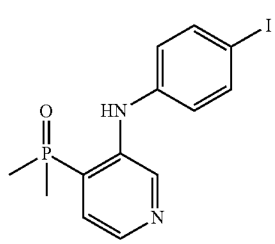 [SMILES: CP(C)(=O)c1ccncc1Nc1ccc(I)cc1] | 4-(Dimethylphosphoryl)-N-(4-iodophenyl)pyridin-3-amine |
| 23 | 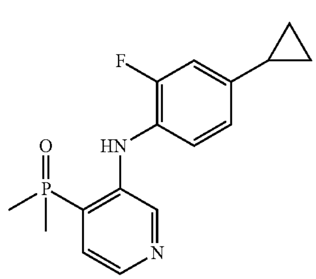 [SMILES: CP(C)(=O)c1ccncc1Nc1ccc(C2CC2)cc1F] | N-(4-Cyclopropyl-2-fluorophenyl)-4-(dimethylphosphoryl)pyridin-3-amine |

TABLE 1-continued

| Synthetic Chemistry Example | Compound Structure | Compound Name |
|---|---|---|
| 24 | 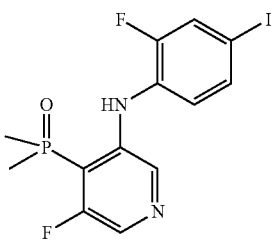 [SMILES: CP(C)(=O)c1c(F)cncc1Nc1ccc(I)cc1F] | 4-(Dimethylphosphoryl)-5-fluoro-N-(2-fluoro-4-iodophenyl)pyridin-3-amine |
| 25 | 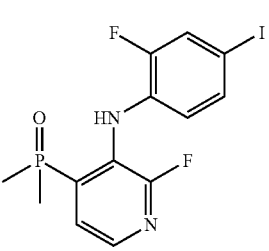 [SMILES: CP(C)(=O)c1ccnc(F)c1Nc1ccc(I)cc1F] | (2-Fluoro-3-((2-fluoro-4-iodophenyl)amino)pyridin-4-yl)dimethylphosphine oxide |
| 26 | 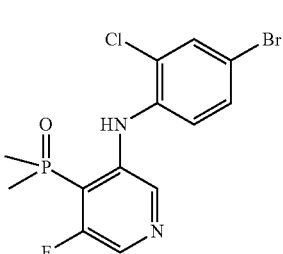 | N-(4-bromo-2-chlorophenyl)-4-(dimethylphosphoryl)-5-fluoropyridin-3-amine |
| 27 | 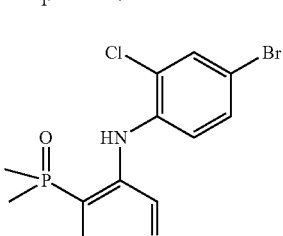 | N-(4-bromo-2-chlorophenyl)-4-(dimethylphosphoryl)pyridin-3-amine |
| 28 | 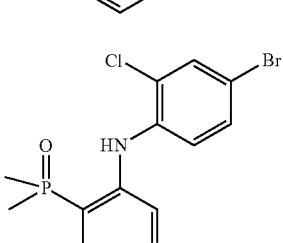 | N-(4-Bromo-2-chlorophenyl)-5-chloro-4-(dimethylphosphoryl)pyridin-3-amine |
| 29 | 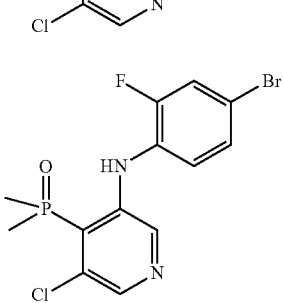 | (3-((4-Bromo-2-fluorophenyl)amino)-5-chloropyridin-4-yl)dimethylphosphine oxide |

TABLE 1-continued

| Synthetic Chemistry Example | Compound Structure | Compound Name |
| --- | --- | --- |
| 30 | 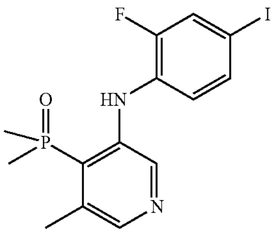 [SMILES: Cc1cncc(Nc2ccc(I)cc2F)c1P(C)(C)=O] | 4-(Dimethylphosphoryl)-N-(2-fluoro-4-iodophenyl)-5-methylpyridin-3-amine |
| 31 | 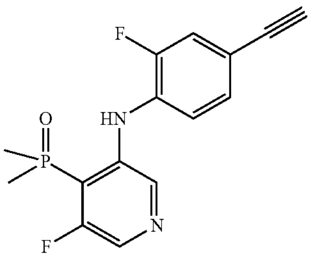 [SMILES: C#Cc1ccc(Nc2cncc(F)c2P(C)(C)=O)c(F)c1] | 4-(Dimethylphosphoryl)-N-(4-ethynyl-2-fluorophenyl)-5-fluoropyridin-3-amine |
| 32 | 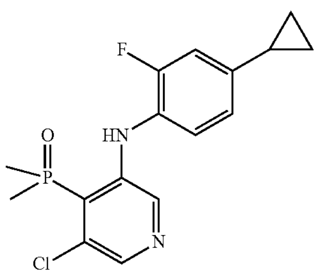 [SMILES: CP(C)(=O)c1c(Cl)cncc1Nc1ccc(C2CC2)cc1F] | (3-Chloro-5-((4-cyclopropyl-2-fluorophenyl)amino)pyridin-4-yl)dimethylphosphine oxide |

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2;

"Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the MEK kinase inhibitory compound described herein is administered as a pure chemical. In other embodiments, the MEK kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one MEK kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), or a pharmaceutically acceptable salt or solvate thereof.

One embodiment provides a method of preparing a pharmaceutical composition comprising mixing a compound of Formula (I), or a pharmaceutically acceptable salt or solvate thereof, and a pharmaceutically acceptable carrier.

In certain embodiments, the MEK kinase inhibitory compound as described by Formula (I), or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1, or a pharmaceutically acceptable salt or solvate thereof.

One embodiment provides a method of preparing a pharmaceutical composition comprising mixing a compound of Table 1, or a pharmaceutically acceptable salt or solvate thereof, and a pharmaceutically acceptable carrier.

In certain embodiments, the MEK kinase inhibitory compound as described by Table 1, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the MEK kinase inhibitory compound as described by Formula (I) or Table 1, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one MEK kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body. One embodiment provides a compound of Formula (I), or a pharmaceutically acceptable salt or solvate thereof, for use in a method of treatment of cancer or neoplastic disease. One embodiment provides a pharmaceutical composition comprising a compound of Formula (I), or a pharmaceutically acceptable salt or solvate thereof, and a pharmaceutically acceptable excipient for use in a method of treatment of cancer or neoplastic disease. One embodiment provides a use of a compound of Formula (I), or a pharmaceutically acceptable salt or solvate thereof, in the manufacture of a medicament for the treatment of cancer or neoplastic disease. Another embodiment provides the use wherein the cancer is selected from lung cancer, breast cancer, skin cancer, melanoma, or leukemia.

In some embodiments is provided a method of treating cancer, in a patient in need thereof, comprising administering to the patient a compound of Formula (I), or a pharmaceutically acceptable salt or solvate thereof. In some embodiments is provided a method of treating cancer, in a patient in need thereof, comprising administering to the patient a pharmaceutical composition comprising a compound of Formula (I), or a pharmaceutically acceptable salt or solvate thereof, and a pharmaceutically acceptable excipient. Another embodiment provides the method wherein the cancer is selected from lung cancer, breast cancer, skin cancer, melanoma, or leukemia.

One embodiment provides a compound of Table 1, or a pharmaceutically acceptable salt or solvate thereof, for use in a method of treatment of the human or animal body. One embodiment provides a compound of Table 1, or a pharmaceutically acceptable salt or solvate thereof, for use in a method of treatment of cancer or neoplastic disease. One embodiment provides a pharmaceutical composition comprising a compound of Table 1, or a pharmaceutically acceptable salt or solvate thereof, and a pharmaceutically acceptable excipient for use in a method of treatment of cancer or neoplastic disease. One embodiment provides a use of a compound of Table 1, or a pharmaceutically acceptable salt or solvate thereof, in the manufacture of a medicament for the treatment of cancer or neoplastic disease. Another embodiment provides the method wherein the cancer is selected from lung cancer, breast cancer, skin cancer, melanoma, or leukemia.

In some embodiments is provided a method of treating cancer, in a patient in need thereof, comprising administering to the patient a compound of Table 1, or a pharmaceutically acceptable salt or solvate thereof. In some embodiments is provided a method of treating cancer, in a patient in need thereof, comprising administering to the patient a pharmaceutical composition comprising a compound of Table 1, or a pharmaceutically acceptable salt or solvate thereof, and a pharmaceutically acceptable excipient. Another embodiment provides the method wherein the cancer is selected from lung cancer, breast cancer, skin cancer, melanoma, or leukemia.

Provided herein is the method wherein the pharmaceutical composition is administered orally. Provided herein is the method wherein the pharmaceutical composition is administered by injection.

One embodiment provides a method of inhibiting a MEK kinase enzyme comprising contacting the MEK kinase enzyme with a compound of Formula (I) or Table 1. Another embodiment provides the method of inhibiting a MEK kinase enzyme, wherein the MEK kinase enzyme is contacted in an in vivo setting. Another embodiment provides the method of inhibiting a MEK kinase enzyme, wherein the MEK kinase enzyme is contacted in an in vitro setting.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the MEK kinase inhibitory compounds disclosed herein are synthesized according to the following examples. As used below, and throughout the description of the invention, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Intermediate 1: Phospholane 1-oxide

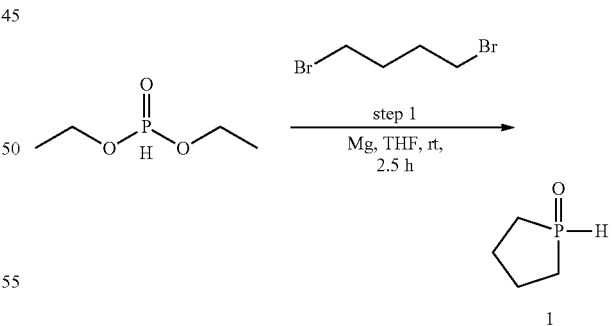

To a stirred mixture of magnesium (3.61 g, 148.440 mmol) in tetrahydrofuran (45 mL) was added 1,3-dibromopropane (14.62 g, 72.41 mmol) in tetrahydrofuran (15 mL) at 15° C. under nitrogen atmosphere. The reaction mixture was stirred for 1.5 h at room temperature. Diethyl phosphonate (5.0 g, 36.20 mmol) in tetrahydrofuran (15 mL) was added the mixture at 15° C. and the reaction mixture was stirred for another 1 h at room temperature. Gradual addition of an ice-cooled solution potassium carbonate (21 g) in water (35 mL) generated a heavy off-white precipitate of magnesium carbonate, which was rapidly filtered off in air and washed with degassed ethanol (50 mL). The filtrate was concentrated under reduced pressure. The residue was purified by silica gel column chromatography, eluted with dichloromethane/methanol (10/1). The fractions contained desired product were combined and concentrated to afford phospholane 1-oxide (1.3 g, 34%) as a colorless oil. $^1$H NMR (400 MHz, CDCl$_3$) δ 8.06 (s, 1H), 2.15-1.94 (m, 4H), 1.94-1.69 (m, 4H).

Intermediate 2: Ethyl(methyl)phosphine oxide

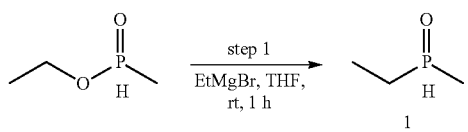

To a stirred solution of 1 M ethylmagnesium bromide in tetrahydrofuran (27.76 mL, 27.76 mmol) was added ethyl methylphosphinate (2.0 g, 18.51 mmol) in tetrahydrofuran (6.0 mL) dropwise at room temperature under nitrogen atmosphere. The reaction mixture was stirred for 1 h at room temperature under nitrogen atmosphere. Gradual addition of a solution potassium carbonate (12 g) in water (20 mL) generated a heavy off-white precipitate of magnesium carbonate, which was rapidly filtered off in air and washed with degassed ethanol (30 mL). The filtrate was concentrated under reduced pressure. The residue was purified by silica gel column chromatography, eluted with dichloromethane/methanol (10/1). The fractions contained desired product was combined and concentrated to afford ethyl(methyl) phosphine oxide (1.0 g, 59%) as a colorless oil. $^1$H NMR (400 MHz, CDCl$_3$) δ 1.94-1.77 (m, 2H), 1.60-1.56 (m, 3H), 1.26-1.17 (m, 3H).

Intermediate 3: (3-Aminopyridin-4-yl)dimethylphosphine oxide

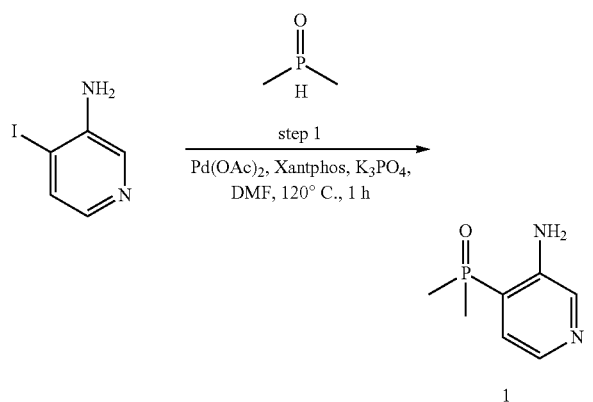

To a stirred mixture of 4-iodopyridin-3-amine (3.0 g, 13.64 mmol), (methylphosphonoyl)methane (1.28 g, 16.36 mmol) and palladium (II) acetate (0.15 g, 0.68 mmol) in N,N-dimethylformamide (30 mL) were added 4,5-bis(diphenylphosphino)-9,9-dimethylxanthene (0.39 g, 0.68 mmol) and potassium phosphate tribasic (3.18 g, 15.00 mmol). The reaction mixture was degassed with nitrogen for three times and stirred for 1 h at 120° C. The resulting mixture was concentrated under reduced pressure. The residue was purified by silica gel column chromatography, eluted with dichloromethane/methanol (10/1). The fractions contained desired product were combined and concentrated to afford 4-(dimethylphosphoryl)pyridin-3-amine (2.18 g, 94%) as a light yellow solid. MS ESI calculated for C$_7$H$_{11}$N$_2$OP [M+H]$^+$, 171.06, found 171.05; $^1$H NMR (400 MHz, CDCl$_3$) δ 8.11 (d, J=5.5 Hz, 1H), 7.96 (dd, J=5.0, 3.6 Hz, 1H), 6.87 (dd, J=13.3, 5.0 Hz, 1H), 5.44 (s, 2H), 1.80 (s, 3H), 1.77 (s, 3H); $^{31}$P NMR (162 MHz, CDCl$_3$) δ 40.73.

The following compounds in Table 2 were prepared using procedures similar to those described in Intermediate 3 using appropriate starting materials.

TABLE 2

| No. | Structure | Name | Exact Mass [M + H]$^+$ |
|---|---|---|---|
| 4 | 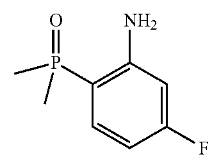 | 2-(Dimethylphosphoryl)-5-fluoroaniline | Calc'd 188.06, found 188.00 |
| 5 | 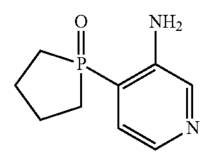 [SMILES: Nc1cnccc1P1(=O)CCCC1] | 1-(3-Aminopyridin-4-yl)phospholane 1-oxide | Calc'd 197.08, found 197.05. |
| 6 | 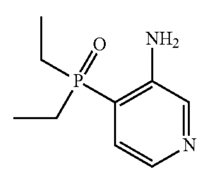 | 4-(Diethylphosphoryl)pyridin-3-amine | Calc'd 199.09, found 199.00 |
| 7 | 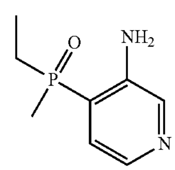 | (3-Aminopyridin-4-yl)(ethyl)(methyl)phosphine oxide | Calc'd 185.08, found 185.00 |

Intermediate 8: 6-(Dimethylphosphoryl)-2,3-difluoroaniline

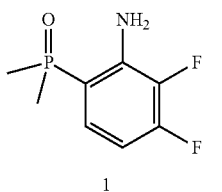

To a stirred mixture of 6-bromo-2,3-difluoroaniline (0.70 g, 3.36 mmol) and (methylphosphonoyl)methane (0.31 g, 4.03 mmol) in N, N-dimethylformamide (1.00 mL) were added palladium acetate (37.78 mg, 0.16 mmol), 4,5-bis(diphenylphosphino)-9,9-dimethylxanthene (97.36 mg, 0.16 mmol) and potassium phosphate (0.79 g, 3.70 mmol) at room temperature. The reaction mixture was stirred at 150° C. for 1 h. The resulting mixture was concentrated under reduced pressure. The residue was purified by silica gel column chromatography, eluted with dichloromethane/methanol (10/1). The fractions contained desired product were combined and concentrated to afford 6-(dimethylphosphoryl)-2,3-difluoroaniline (200 mg, 29%) as a grey solid. MS ESI calculated for $C_8H_{10}F_2NOP$ $[M+H]^+$, 206.05, found 206.05; $^1H$ NMR (400 MHz, $CDCl_3$) δ 6.54-6.50 (m, 1H), 5.26 (s, 2H), 1.80 (d, J=12.1 Hz, 6H); $^{19}F$ NMR (377 MHz, $CDCl_3$) δ −132.99 (1F), −160.67 (1F).

The following compounds in Table 3 were prepared using procedures similar to those described in Intermediate 8 using appropriate starting materials.

TABLE 3

| No. | Structure | Name | Exact Mass $[M + H]^+$ |
|---|---|---|---|
| 9 | (structure) | 5-Chloro-4-(dimethylphosphoryl)pyridin-3-amine | Calc'd 205.02, 207.02, found 204.95, 206.95 |
| 10 | (structure) | (5-Amino-2-fluoropyridin-4-yl)dimethylphosphine oxide | Calc'd 189.05, found 189.15 |

Example 1: 4-(Dimethylphosphoryl)-N-(2-fluoro-4-iodophenyl)pyridin-3-amine

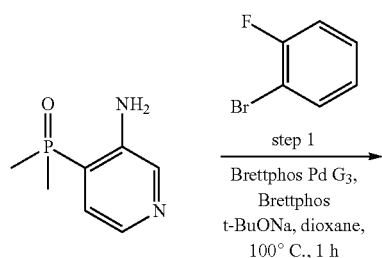

step 1
Brettphos Pd G3,
Brettphos
t-BuONa, dioxane,
100° C., 1 h

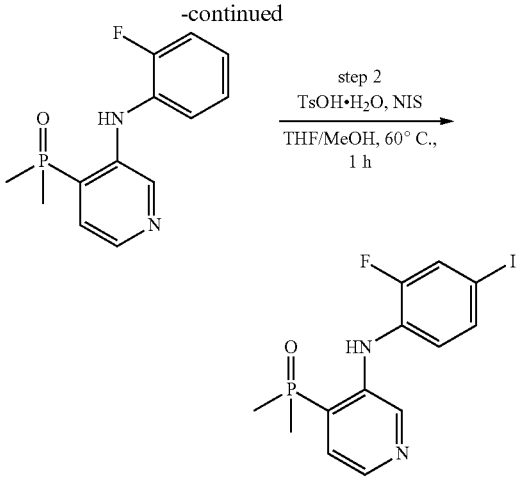

Step 1. 4-(Dimethylphosphoryl)-N-(2-fluorophenyl)pyridin-3-amine

To a stirred mixture of 4-(dimethylphosphoryl)pyridin-3-amine (2.18 g, 12.81 mmol), 1-bromo-2-fluorobenzene (3.36 g, 19.22 mmol), methanesulfonato2-dicyclohexylphosphino-3,6-dimethoxy-2'-4'-6'-tri-i-propyl-1,1'-bipheny)(2'-amino-1,1'-biphenyl-2-yl)palladium(II) (BrettPhos Pd G3) (1.16 g, 1.28 mmol) and 2-(dicyclohexylphosphino)-3,6-dimethoxy-2'-4'-6'-tri-i-propyl-1,1'-biphenyl (BrettPhos) (1.38 g, 2.56 mmol) in 1,4-dioxane (25 mL) was added sodium tert-butoxide (3.69 g, 38.44 mmol). The reaction mixture was degassed with nitrogen for three times and stirred for 1 h at 100° C. The resulting mixture was concentrated under reduced pressure. The residue was purified by silica gel column chromatography, eluted with dichloromethane/methanol (10/1). The fractions contained desired product were combined and concentrated to afford 4-(dimethylphosphoryl)-N-(2-fluorophenyl)pyridin-3-amine (2.6 g, 77%) as a yellow oil. MS ESI calculated for $C_{13}H_{14}FN_2OP$ $[M+H]^+$, 265.08, found 265.00; $^1H$ NMR (400 MHz, $CDCl_3$) δ 8.95 (s, 1H), 8.41 (d, J=5.3 Hz, 1H), 8.12 (t, J=4.3 Hz, 1H), 7.36 (t, J=7.7 Hz, 1H), 7.16-7.04 (m, 4H), 1.89 (s, 3H), 1.86 (s, 3H); $^{19}F$ NMR (377 MHz, CDCl3) δ −123.53.

Step 2. 4-(Dimethylphosphoryl)-N-(2-fluoro-4-iodophenyl)pyridin-3-amine

To a stirred mixture of 4-(dimethylphosphoryl)-N-(2-fluorophenyl)pyridin-3-amine (2.6 g, 9.84 mmol) in tetrahydrofuran (25 mL) and methanol (25 mL) were added p-toluenesulfonic acid monohydrate (5.24 g, 27.55 mmol) and N-iodosuccinimide (6.64 g, 29.52 mmol) at room temperature. The reaction mixture was stirred for 1 h at 60° C. The resulting mixture was concentrated under reduced pressure. The residue was purified by silica gel column chromatography, eluted with dichloromethane/ethanol (10/1) to afford crude product (3.3 g) which was further purified by reverse flash chromatography with the following conditions: column, C18 silica gel; mobile phase: acetonitrile in water (Plus 10 mmol/L $NH_4HCO_3$), 15% to 50% gradient in 30 min; detector: UV 254/220 nm. The fractions contained desired product were combined and concentrated to afford 4-(dimethylphosphoryl)-N-(2-fluoro-4-iodophenyl)pyridin-3-amine (1.08 g, >98% purity, 28%) as an off-white solid and ~1 g 95% purity product. MS ESI calculated for $C_{13}H_{13}FIN_2OP$ [M+H]$^+$, 390.98, found 391.05; $^1$H NMR (400 MHz, DMSO-d$_6$) δ 9.35 (s, 1H), 8.47 (d, J=5.2 Hz, 1H), 8.20-8.18 (m, 1H), 7.69-7.66 (m, 1H), 7.50-7.45 (m, 2H), 7.26 (t, J=8.6 Hz, 1H), 1.83 (s, 3H), 1.80 (s, 3H); $^{19}$F NMR (376 MHz, DMSO-d$_6$) δ −124.70.

The following compounds in Table 4 were prepared using procedures similar to those described in Example 1 using appropriate starting materials.

TABLE 4

| No. | Structure | Name | Exact Mass [M + H]$^+$ |
|---|---|---|---|
| 2 | 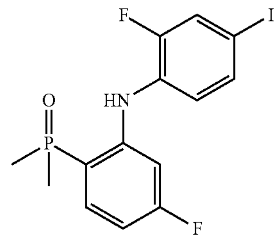 [SMILES: CP(C)(=O)c1ccc(F)cc1Nc1ccc(I)cc1F] | 2-(Dimethylphosphoryl)-5-fluoro-N-(2-fluoro-4-iodophenyl)-aniline | Calc'd 407.97, found 407.90 |
| 3 | 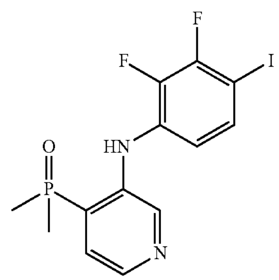 [SMILES: CP(C)(=O)c1ccncc1Nc1ccc(I)c(F)c1F] | N-(2,3-Difluoro-4-iodophenyl)-4-(dimethylphosphoryl)-pyridin-3-amine | Calc'd 408.97, found 409.90 |
| 4 | 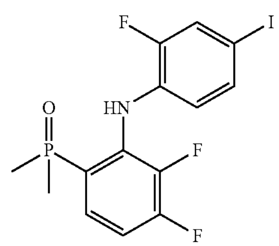 [SMILES: CP(C)(=O)c1ccc(F)c(F)c1Nc1ccc(I)cc1F] | 6-(Dimethylphosphoryl)-2,3-difluoro-N-(2-fluoro-4-iodophenyl)-aniline | Calc'd 425.97, found 425.80 |
| 5 | 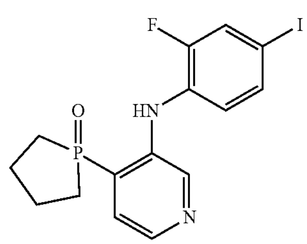 [SMILES: O=P1(c2ccncc2Nc2ccc(I)cc2F)CCCC1] | 1-(3-((2-Fluoro-4-iodophenyl)-amino)-pyridin-4-yl)phospholane 1-oxide | Calc'd 417.00, found 417.00 |
| 6 | 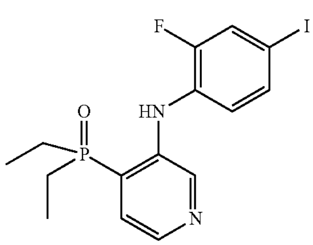 [SMILES: CCP(=O)(CC)c1ccncc1Nc1ccc(I)cc1F] | 4-(Diethylphosphoryl)-N-(2-fluoro-4-iodophenyl)-pyridin-3-amine | Calc'd 419.01, found 419.40 |
| 7 | | 4-[Ethyl(methyl)phosphoryl]-N-(2-fluoro-4-iodophenyl)-pyridin-3-amine | Calc'd 405.00, found 405.00 |
| 13 | | 5-Chloro-4-(dimethylphosphoryl)-N-(2-fluoro-4-iodophenyl)-pyridin-3-amine | Calc'd 424.94, found 424.95 |
| 21 | | (2-Fluoro-5-((2-fluoro-4-iodophenyl)-amino)pyridin-4-yl)dimethylphosphine oxide | Calc'd 408.97, found 409.00 |
| 22 | | 4-(Dimethylphosphoryl)-N-(4-iodophenyl)-pyridin-3-amine | Calc'd 372.99, found 372.95 |

Example 8 & 9: (R)-4-[Ethyl(methyl)phosphoryl]-N-(2-fluoro-4-iodophenyl)pyridin-3-amine and (S)-4-[ethyl(methyl)phosphoryl]-N-(2-fluoro-4-iodophenyl)pyridin-3-amine -continued

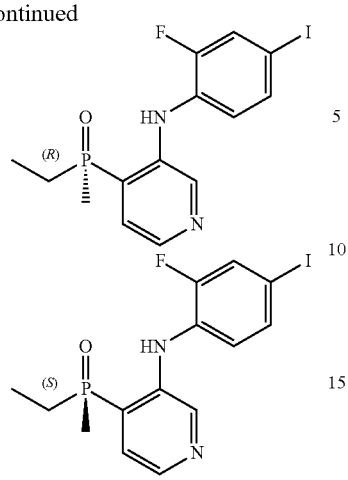

The 4-[ethyl(methyl)phosphoryl]-N-(2-fluoro-4-iodophenyl)pyridin-3-amine (54 mg) was purified by Prep-chiral-HPLC with the following conditions: Column: CHIRALPAK IE, 2×25 cm; Mobile Phase A: hexanes (0.5% 2 M NH$_3$-MeOH)—HPLC, Mobile Phase B: EtOH:DCM=1:1-HPLC; Flow rate: 20 mL/min; Gradient: 30% B to 30% B in 14 min; Wave Length: 220/254 nm; RT1 (min): 10.92; RT2 (min): 12.85; Sample Solvent: MeOH:DCM=1:1-HPLC; Injection Volume: 0.3 mL. The faster peak (RT1: 10.92 min) contained desired product were combined and concentrated to afford one enantiomer (absolute chiral configuration was not determined) (19.9 mg, 36%) as a light yellow semi-solid. MS ESI calculated for C$_{14}$H$_{15}$FIN$_2$OP [M+H]$^+$, 405.00, found 405.00; $^1$H NMR (400 MHz, DMSO-d$_6$) δ 9.45 (s, 1H), 8.47 (d, J=5.0 Hz, 1H), 8.18 (t, J=5.0 Hz, 1H), 7.69-7.66 (m, 1H), 7.49-7.42 (m, 2H), 7.27 (t, J=8.6 Hz, 1H), 2.08-2.00 (m, 2H), 1.82 (d, J=13.6 Hz, 3H) 1.06-0.98 (m, 3H); $^{19}$F NMR (376 MHz, DMSO-d$_6$) δ −124.71.

The slower peak (RT2: 12.85 min) contained desired product were combined and concentrated to afford second enantiomer (absolute chiral configuration was not determined) (19.8 mg, 36%) as a light yellow semi-solid. MS ESI calculated for C$_{14}$H$_{15}$FIN$_2$OP [M+H]$^+$, 405.00, found 405.00; $^1$H NMR (400 MHz, DMSO-d$_6$) δ 9.45 (s, 1H), 8.47 (d, J=5.0 Hz, 1H), 8.18 (t, J=5.0 Hz, 1H), 7.69-7.66 (m, 1H), 7.49-7.42 (m, 2H), 7.27 (t, J=8.6 Hz, 1H), 2.08-2.00 (m, 2H), 1.82 (d, J=13.6 Hz, 3H) 1.06-0.98 (m, 3H). $^{19}$F NMR (376 MHz, DMSO-d$_6$) δ −124.68.

Example 10: N-(4-Bromo-2-fluorophenyl)-4-(dimethylphosphoryl)pyridin-3-amine

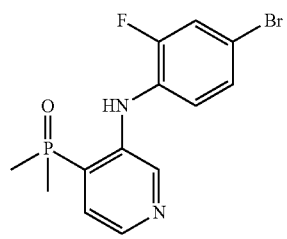 [SMILES: CP(C)(=O)c1ccncc1Nc1ccc(Br)cc1F]

To a stirred mixture of 4-(dimethylphosphoryl)pyridin-3-amine (0.25 g, 1.46 mmol) and 4-bromo-2-fluoro-1-iodobenzene (0.66 g, 2.20 mmol) in 1,4-dioxane (2.50 mL) were added 2-(dicyclohexylphosphino)-3,6-dimethoxy-2'-4'-6'-tri-i-propyl-1,1'-biphenyl (BrettPhos) (0.15 g, 0.29 mmol), methanesulfonato2-dicyclohexylphosphino-3,6-dimethoxy-2'-4'-6'-tri-i-propyl-1,1'-bipheny)(2'-amino-1,1'-biphenyl-2-yl)palladium(II) (BrettPhos Pd G$_3$) (0.13 g, 0.14 mmol) and sodium tert-butoxide (0.42 g, 4.40 mmol) in portions at room temperature. The reaction mixture was degassed with nitrogen for three times and stirred at 100° C. for 1 h. The resulting mixture was concentrated under reduced pressure. The residue was purified by reverse phase flash chromatography with the following conditions: Column: Xselect CSH C18 OBD Column 30×150 mm 5 μm; Mobile Phase A: Water (10 mmol/L ammonium bicarbonate), Mobile Phase B: acetonitrile; Flow rate: 60 ml/min; Gradient: 27% B to 37% B in 11 min; Wavelength: 254 nm. The fractions contained desired product were combined and concentrated to afford N-(4-bromo-2-fluorophenyl)-4-(dimethylphosphoryl)pyridin-3-amine (10 mg, 2%) as a light yellow oil. MS ESI calculated for C$_{13}$H$_{13}$BrFN$_2$OP [M+H]$^+$, 342.99, 344.99, found 342.95, 344.95; $^1$H NMR (400 MHz, DMSO-d$_6$) δ 9.37 (s, 1H), 8.46 (d, J=5.2 Hz, 1H), 8.19 (dd, J=4.9, 3.2 Hz, 1H), 7.61 (dd, J=10.8, 2.2 Hz, 1H), 7.53-7.38 (m, 2H), 7.35 (dd, J=8.8, 2.2 Hz, 1H), 1.82 (d, J=13.7 Hz, 6H); $^{19}$F NMR (377 MHz, DMSO-d$_6$) δ −123.94 (1F).

The following compounds in Table 5 were prepared using procedures similar to those described in Example 10 using appropriate starting materials.

TABLE 5

| No. | Structure | Name | Exact Mass [M + H]$^+$ |
|---|---|---|---|
| 11 | 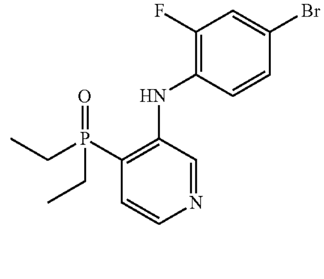 [SMILES: CCP(=O)(CC)c1ccncc1Nc1ccc(Br)cc1F] | N-(4-bromo-2-fluorophenyl)-4-(diethylphosphoryl)pyridin-3-amine | Calc'd 371.02, 373.02, found 370.95, 372.95 |

TABLE 5-continued

| No. | Structure | Name | Exact Mass [M + H]+ |
|---|---|---|---|
| 12 | 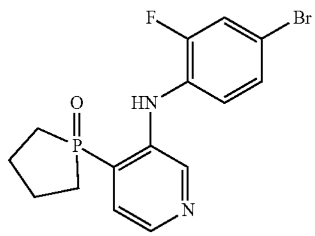 [SMILES: O=P1(c2ccncc2Nc2ccc(Br)cc2F)CCCC1] | 1-(3-((4-Bromo-2-fluorophenyl)amino)pyridin-4-yl)phospholane 1-oxide | Calc'd 369.01, 371.01, found 369.00, 371.00 |
| 26 | 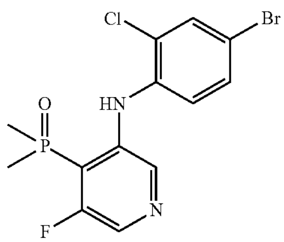 [SMILES: CP(C)(=O)c1c(F)cncc1Nc1ccc(Br)cc1Cl] | N-(4-bromo-2-chlorophenyl)-4-(dimethylphosphoryl)-5-fluoropyridin-3-amine | Calc'd 376.95, 378.95, found 376.95, 378.95 |
| 27 | 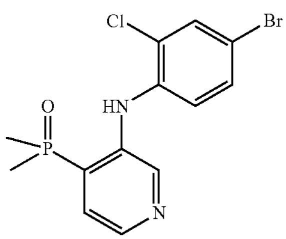 [SMILES: CP(C)(=O)c1ccncc1Nc1ccc(Br)cc1Cl] | N-(4-bromo-2-chlorophenyl)-4-(dimethylphosphoryl)pyridin-3-amine | Calc'd 358.96, 360.96, found 359.00, 361.00 |
| 28 | 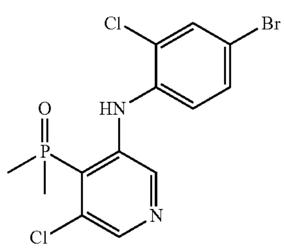 [SMILES: CP(C)(=O)c1c(Cl)cncc1Nc1ccc(Br)cc1Cl] | N-(4-Bromo-2-chlorophenyl)-5-chloro-4-(dimethylphosphoryl)pyridin-3-amine | Calc'd 392.92, 394.92, found 392.90, 394.90 |
| 29 | 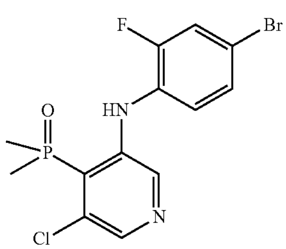 [SMILES: CP(C)(=O)c1c(Cl)cncc1Nc1ccc(Br)cc1F] | (3-((4-Bromo-2-fluorophenyl)amino)-5-chloropyridin-4-yl)dimethylphosphine oxide | Calc'd 376.95, 378.95, found 376.90, 378.90 |

Example 14: (3-((4-ethynyl-2-fluorophenyl)amino)pyridin-4-yl)dimethylphosphine oxide

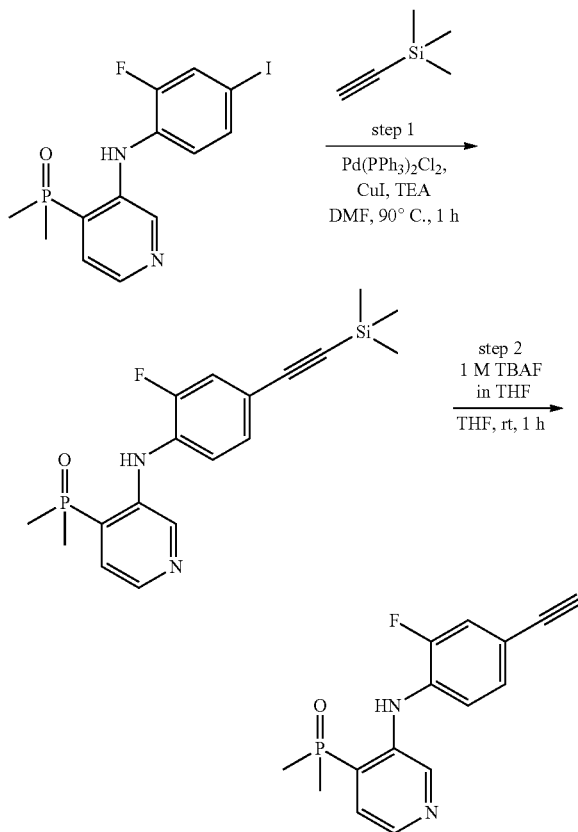

Step 1. (3-((2-Fluoro-4-((trimethylsilyl)ethynyl)phenyl)amino)pyridin-4-yl)dimethylphosphine oxide To a stirred mixture of 4-(dimethylphosphoryl)-N-(2-fluoro-4-iodophenyl)pyridin-3-amine (0.30 g, 0.77 mmol), trimethylsilylacetylene (0.23 g, 2.31 mmol), trans-dichlorobis(triphenylphosphine)palladium (53.97 mg, 0.08 mmol) and cuprous iodide (29.29 mg, 0.15 mmol) in N,N-dimethylformamide (3.00 mL) was added triethylamine (0.23 g, 2.31 mmol) at room temperature. The reaction mixture was degassed with nitrogen for three times and stirred for 1 h at 90° C. The resulting mixture was concentrated under reduced pressure. The residue was purified by silica gel column chromatography, eluted with dichloromethane/methanol (10/1). The fractions contained desired product were combined and concentrated to afford (3-((2-fluoro-4-((trimethylsilyl)ethynyl)phenyl)amino)pyridin-4-yl)dimethylphosphine oxide (0.25 g, 90%/) as a brown solid. MS ESI calculated for $C_{18}H_{22}FN_2OPSi$ $[M+H]^+$, 361.12, found 361.10.

Step 2: (3-((4-Ethynyl-2-fluorophenyl)amino)pyridin-4-yl)dimethylphosphine oxide To a stirred solution of (3-((2-fluoro-4-((trimethylsilyl)ethynyl)phenyl)amino)pyridin-4-yl)dimethylphosphine oxide (0.27 g, 0.75 mmol) in tetrahydrofuran (3.00 mL) was added TBAF in tetrahydrofuran (1.12 mL, 1 M) dropwise at room temperature. The reaction mixture was stirred for 1 h at room temperature. The resulting mixture was concentrated under reduced pressure. The residue was purified by silica gel column chromatography, eluted with dichloromethane/methanol (10/1) to afford the crude product. The crude product (0.20 g) was purified by Prep-HPLC with the following conditions: Column: XBridge Prep OBD C18 Column, 30×150 mm, 5 μm; Mobile phase A: Water (10 mmol/L $NH_4HCO_3$), Mobile phase B: ACN; Flow rate: 60 mL/min; Gradient: 21% B to 31% B in 8 min, 31% B; Wave length: 254 nm; RT: 7 min. The fractions contained desired product were combined and concentrated to afford (3-((4-ethynyl-2-fluorophenyl)amino)pyridin-4-yl)dimethylphosphine oxide (60.90 mg, 28%) as a light yellow semi-solid. MS ESI calculated for $C_{15}H_{14}FN_2OP$ $[M+H]^+$, 289.08, found 289.05; $^1H$ NMR (400 MHz, DMSO-$d_6$) δ 9.51 (d, J=1.7 Hz, 1H), 8.57 (d, J=5.1 Hz, 1H), 8.23 (dd, J=4.9, 3.2 Hz, 1H), 7.51 (dd, J=13.2, 4.9 Hz, 1H), 7.46-7.36 (m, 2H), 7.26 (dd, J=8.3, 1.9 Hz, 1H), 4.18 (s, 1H), 1.82 (d, J=13.8 Hz, 6H).

The following compounds in Table 6 were prepared using procedures similar to those described in Example 14 using appropriate starting materials.

TABLE 6

| No. | Structure | Name | Exact Mass $[M + H]^+$ |
|---|---|---|---|
| 15 | 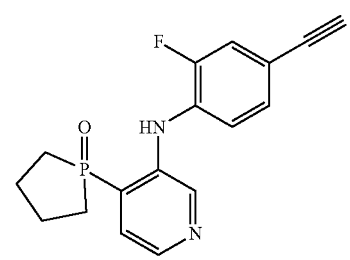 [SMILES: C#Cc1ccc(Nc2cnccc2P2(=O)CCCC2)c(F)c1] | 1-(3-((4-Ethynyl-2-fluorophenyl)amino)-pyridin-4-yl)phospholane 1-oxide | Calc'd 315.10, found 315.10 |
| 18 | 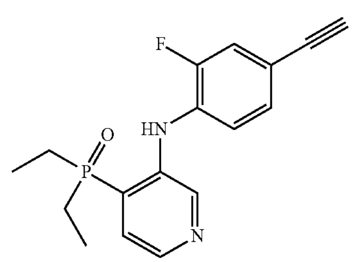 [SMILES: C#Cc1ccc(Nc2cnccc2P(=O)(CC)CC)c(F)c1] | 4-(Diethylphosphoryl)-N-(4-ethynyl-2-fluorophenyl)-pyridin-3-amine | Calc'd 317.11, found 317.00 |
| 31 | 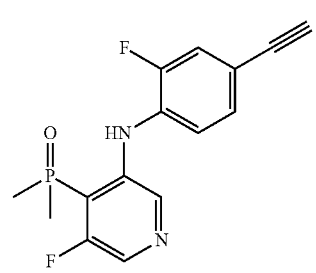 [SMILES: C#Cc1ccc(Nc2cncc(F)c2P(C)(C)=O)c(F)c1] | 4-(Dimethylphosphoryl)-N-(4-ethynyl-2-fluorophenyl)-5-fluoropyridin-3-amine | Calc'd 307.07, found 307.00 |

Example 16 & 17: N-(4-Bromo-2-fluorophenyl)-4-[(R)-ethyl(methyl)phosphoryl]pyridin-3-amine & N-(4-Bromo-2-fluorophenyl)-4-[(S)-ethyl(methyl)phosphoryl]pyridin-3-amine

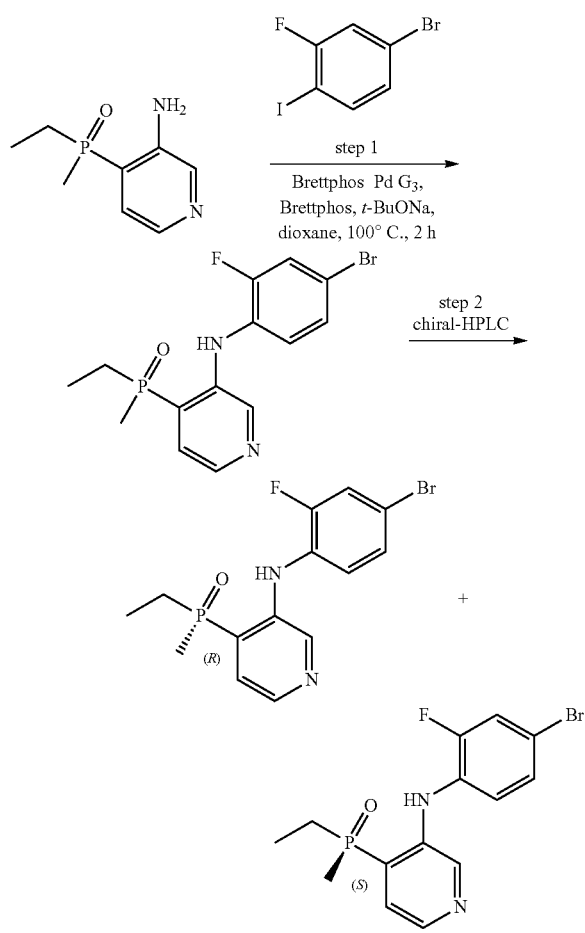

Step 1. N-(4-Bromo-2-fluorophenyl)-4-[ethyl(methyl)phosphoryl]pyridin-3-amine To a stirred mixture of 4-[ethyl(methyl)phosphoryl]pyridin-3-amine (180 mg, 0.98 mmol), methanesulfonato2-dicyclohexylphosphino-3,6-dimethoxy-2'-4'-6'-tri-i-propyl-1,1'-bipheny)(2'-amino-1,1'-biphenyl-2-yl)palladium(II) (BrettPhos Pd G3) (CAS:1470372-59-8) (88.59 mg, 0.10 mmol), 2-(dicyclohexylphosphino)-3,6-dimethoxy-2'-4'-6'-tri-i-propyl-1,1'-biphenyl (BrettPhos) (CAS:1070663-78-3) (104.92 mg, 0.20 mmol) and sodium tert-butoxide (281.77 mg, 2.93 mmol) in 1,4-dioxane (1.8 mL) was added 4-bromo-2-fluoro-1-iodobenzene (441.10 mg, 1.47 mmol) at room temperature. The reaction mixture was degassed with nitrogen for three times and stirred for 2 h at 100° C. The resulting mixture was concentrated under reduced pressure. The residue was purified by silica gel column chromatography, eluted with dichloromethane/methanol (10/1) to afford the crude product. The crude product was purified by reverse flash chromatography with the following conditions: A: Water (Plus 10 mmol/L $NH_4HCO_3$), Mobile Phase B: ACN; Flow rate: 60 mL/min; Gradient: 28% B to 37% B in 8 min, 37% B; Wave Length: 254 nm; RT1 (min): 7. The fractions contained desired product were combined and concentrated to afford N-(4-bromo-2-fluorophenyl)-4-[ethyl(methyl)phosphoryl]pyridin-3-amine (79 mg, 22%) as a colorless oil. MS ESI calculated for $C_{14}H_{15}BrFN_2OP$ [M+H]$^+$, 357.01, 359.01, found 357.00, 359.00.

Step 2: N-(4-Bromo-2-fluorophenyl)-4-[(R)-ethyl(methyl)phosphoryl]pyridin-3-amine & N-(4-Bromo-2-fluorophenyl)-4-[(S)-ethyl(methyl)phosphoryl]pyridin-3-amine The (N-(4-bromo-2-fluorophenyl)-4-[ethyl(methyl)phosphoryl]pyridin-3-amine) (79 mg) was purified by Prep-HPLC with the following conditions: Column: CHIRALPAK IE, 2×25 cm, 5 μm; Mobile Phase A: methyl tert-butyl ether (0.5% 2 M $NH_3$-methyl alcohol)—HPLC, Mobile Phase B: ethyl alcohol:DCM=1:1-HPLC; Flow rate: 20 mL/min; Gradient: 20% B to 20% B in 12 min; Wave Length: 220/254 nm; RT1 (min): 9.29; RT2 (min): 11.34. The faster peak (RT1: 9.29 min) contained desired product were combined and concentrated to afford one enantiomer (19.5 mg, 25%) as a colorless oil. MS ESI calculated for $C_{14}H_{15}BrFN_2OP$ [M+H]$^+$, 357.01, 359.01, found 357.15, 359.15; $^1$H NMR (400 MHz, DMSO-$d_6$) δ 9.44 (s, 1H), 8.46 (d, J=5.1 Hz, 1H), 8.18 (dd, J=4.9, 3.2 Hz, 1H), 7.60 (dd, J=10.7, 2.2 Hz, 1H), 7.49-7.38 (m, 2H), 7.35-7.29 (m, 1H), 2.04-1.96 (m, 2H), 1.82 (d, J=13.3 Hz, 3H), 1.03-0.98 (m, 3H).; $^{19}$F NMR (376 MHz, DMSO-$d_6$) δ −123.83 (1F).

The slower peak contained desired product were combined and concentrated to afford second enantiomer (18 mg, 23%) as a colorless oil. MS ESI calculated for $C_{14}H_{15}BrFN_2OP$ [M+H]$^+$, 357.01, 359.01, found 357.15, 359.15; $^1$H NMR (400 MHz, DMSO-$d_6$) δ 9.44 (s, 1H), 8.46 (d, J=5.1 Hz, 1H), 8.18 (dd, J=4.9, 3.2 Hz, 1H), 7.60 (dd, J=10.7, 2.2 Hz, 1H), 7.49-7.38 (m, 2H), 7.35-7.28 (m, 1H), 2.04-1.95 (m, 2H), 1.82 (d, J=13.3 Hz, 3H), 1.04-0.95 (, 3H).; $^{19}$F NMR (376 MHz, DMSO-$d_6$) δ −123.83 (1F).

Example 19 & 20: 4-[(R)-Ethyl(methyl)phosphoryl]-N-(4-ethynyl-2-fluorophenyl)pyridin-3-amine & 4-[(S)-Ethyl(methyl)phosphoryl]-N-(4-ethynyl-2-fluorophenyl)pyridin-3-amine

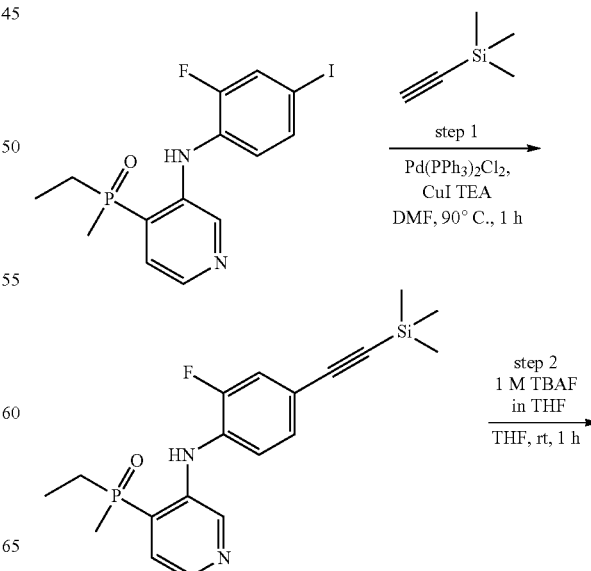

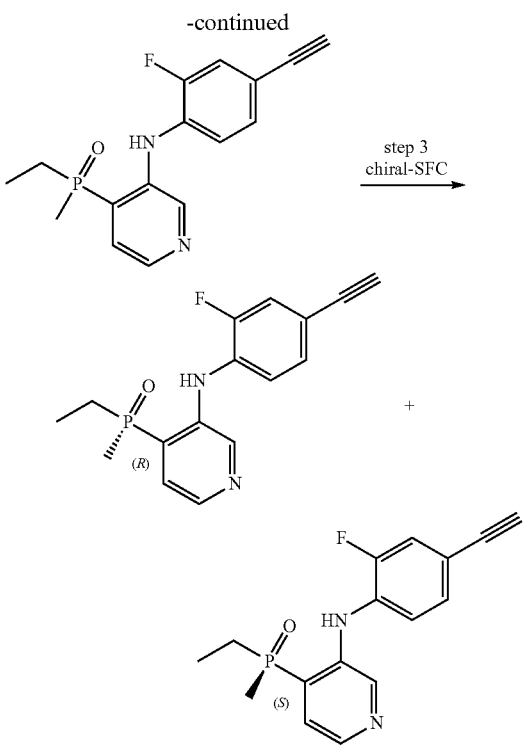

Step 1. 4-[Ethyl(methyl)phosphoryl]-N-{2-fluoro-4-[2-(trimethylsilyl)ethynyl]phenyl}pyridin-3-amine To a stirred mixture of 4-[ethyl(methyl)phosphoryl]-N-(2-fluoro-4-iodophenyl)pyridin-3-amine (400 mg, 0.99 mmol) and CuI (37.70 mg, 0.20 mmol) in DMF (4 mL) were added trimethylsilylacetylene (0.42 mL, 2.97 mmol) and triethylamine (0.41 mL, 2.97 mmol) dropwise at room temperature. The reaction mixture was degassed with nitrogen for three times and stirred for 1 h at 90° C. The resulting mixture was concentrated under reduced pressure. The residue was purified by silica gel column chromatography, eluted with dichloromethane/methanol (10/1). The fractions contained desired product were combined and concentrated to afford 4-[ethyl(methyl)phosphoryl]-N-{2-fluoro-4-[2-(trimethylsilyl)ethynyl]phenyl}pyridin-3-amine (270 mg, 73%) as a brown solid. MS ESI calculated for $C_{19}H_{24}FN_2OPSi$ [M+H]$^+$, 375.15, found 375.00.

Step 2. 4-[Ethyl(methyl)phosphoryl]-N-(4-ethynyl-2-fluorophenyl)pyridin-3-amine

To a stirred solution of 4-[ethyl(methyl)phosphoryl]-N-{2-fluoro-4-[2 (trimethylsilyl)ethynyl]phenyl}pyridin-3-amine (230 mg, 0.61 mmol) in tetrahydrofuran (2.3 mL) was added TBAF (0.92 mL, 0.92 mmol) dropwise at 0° C. The reaction mixture was stirred for 1 h at room temperature under. The resulting mixture was concentrated under reduced pressure. The residue was purified by reverse phase flash chromatography with the following conditions: Column: WelFlash™ C18-I, 20-40 μm, 120 g; Eluent A: Water (Plus 10 mmol/L $NH_4HCO_3$); Eluent B: ACN; Gradient: 25%-45% B in 25 min; Flow rate: 60 m/min; Detector: 220/254 nm. The fractions contained desired product were combined and concentrated to afford 4-[ethyl(methyl)phosphoryl]-N-(4-ethynyl-2-fluorophenyl)pyridin-3-amine (90 mg, 48%) as a yellow solid. MS ESI calculated for $C_{16}H_{16}FN_2OP$ [M+H]$^+$, 303.10, found 303.00.

Step 3. 4-[(R)-Ethyl(methyl)phosphoryl]-N-(4-ethynyl-2-fluorophenyl)pyridin-3-amine & 4-[(S)-Ethyl(methyl)phosphoryl]-N-(4-ethynyl-2-fluorophenyl)pyridin-3-amine The 4-[ethyl(methyl)phosphoryl]-N-(4-ethynyl-2-fluorophenyl)pyridin-3-amine (90 mg, 0.30 mmol) was purified by Prep-HPLC with the following conditions: Column: CHIRALPAK IE, 2×25 cm, 5 μm; Mobile Phase A: Hex (0.5% 2 M $NH_3$-MeOH)—HPLC, Mobile Phase B: methyl alcohol: dichloromethane=1:1-HPLC; Flow rate: 20 m/min; Gradient: 30% B to 30% B in 13 min; Wave Length: 220/254 nm; RT1 (min): 10.21; RT2 (min): 11.86. The faster peak contained desired product were combined and concentrated to afford one enantiomer (12.2 mg, 13%) as a yellow solid. MS ESI calculated for $C_{16}H_{16}FN_2OP$ [M+H]$^+$, 303.10, found 303.05; $^1$H NMR (400 MHz, DMSO-d$_6$) δ 9.61 (s, 1H), 8.58 (d, J=5.0 Hz, 1H), 8.23 (dd, J=4.9, 3.1 Hz, 1H), 7.52-7.37 (m, 3H), 7.26 (d, J=8.0 Hz, 1H), 4.19 (s, 1H), 2.04-1.98 (m, 2H), 1.83 (d, J=13.4 Hz, 3H), 1.02-0.95 (m, 3H); $^{19}$F NMR (376 MHz, DMSO-d$_6$) δ −127.61 (1F); $^{31}$P NMR (162 MHz, DMSO-d$_6$) δ 49.17 (1P).

The slower peak contained desired product were combined and concentrated to afford second enantiomer (23 mg, 25%) as a yellow solid. MS ESI calculated for $C_{16}H_{16}FN_2OP$ [M+H]$^+$, 303.10, found 303.05; $^1$H NMR (400 MHz, DMSO-s) S 9.61 (s, 1H), 8.58 (d, J=5.0 Hz, 1H), 8.23 (dd, J=4.9, 3.1 Hz, 1H), 7.52-7.37 (m, 3H), 7.26 (d, J=8.0 Hz, 1H), 4.19 (s, 1H), 2.06-2.00 (m, 2H), 1.83 (d, J=13.4 Hz, 3H), 1.04-0.99 (m, 3H); $^{19}$F NMR (376 MHz, DMSO-d$_6$) δ −127.61 (1F); $^{31}$P NMR (162 MHz, DMSO-d$_6$) δ 48.956 (1P).

Example 23: N-(4-Cyclopropyl-2-fluorophenyl)-4-(dimethylphosphoryl)pyridin-3-amine

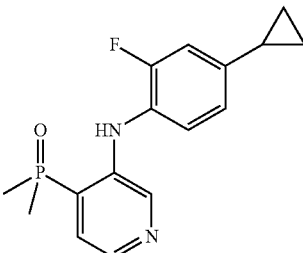

To a stirred solution of 4-(dimethylphosphoryl)-N-(2-fluoro-4-iodophenyl)pyridin-3-amine (200 mg, 0.51 mmol) and cyclopropylboronic acid (132.11 mg, 1.54 mmol) and Dichlorobis(triphenylphosphine)palladium(II) (83.52 mg, 0.10 mmol) and Potassium phosphate tribasic (326.45 mg, 1.54 mmol) in dioxane (2 mL) and water (0.2 mL) at room temperature. The reaction mixture was degassed with nitrogen for three times and stirred for 1 h at 90° C. The resulting mixture was concentrated under reduced pressure. The residue was purified by silica gel column chromatography, eluted with Dichloromethane/Methanol (12/1). The crude product was purified by Prep-HPLC with the following conditions Column: XBridge Prep OBD C18 Column, 30×150 mm, 5 μm; Mobile Phase A: Water (Plus 10 mmol/L $NH_4HCO_3$), Mobile Phase B: ACN; Flow rate: 60 mL/min;

Gradient: 23% B to 33% B in 8 min, 33% B; Wave Length: 254 nm. The fractions contained desired product were combined and concentrated to afford N-(4-cyclopropyl-2-fluorophenyl)-4-(dimethylphosphoryl)pyridin-3-amine (50.3 mg) as an off-white solid. MS ESI calculated for $C_{16}H_{18}FN_2OP$ [M+H]$^+$, 305.11, found 305.10; $^1$H NMR (400 MHz, DMSO-d$_6$) δ 8.28-8.22 (m, 1H), 8.08 (dd, J=4.9, 3.3 Hz, 1H), 7.40-7.36 (m, 1H), 7.30 (t, J=8.5 Hz, 1H), 7.00 (dd, J=12.5, 2.1 Hz, 1H), 6.93 (dd, J=8.2, 2.1 Hz, 1H), 1.99-1.87 (m, 1H), 1.81 (d, J=13.7 Hz, 6H), 1.01-0.89 (m, 2H), 0.73-0.64 (m, 2H).

The following compounds in Table 7 were prepared using procedures similar to those described in Example 23 using appropriate starting materials.

TABLE 7

| No. | Structure | Name | Exact Mass [M + H]$^+$ |
|---|---|---|---|
| 32 | 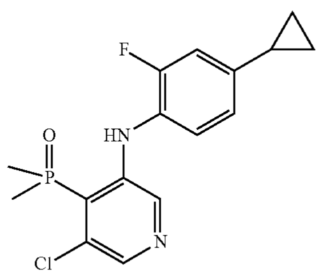 [SMILES: CP(C)(=O)c1c(Cl)cncc1Nc1ccc(C2CC2)cc1F] | (3-Chloro-5-((4-cyclopropyl-2-fluorophenyl)-amino)-pyridin-4-yl)dimethyl-phosphine oxide | Calc'd 339.08, 341.08, found 338.95, 340.95 |

Example 24: 4-(Dimethylphosphoryl)-5-fluoro-N-(2-fluoro-4-iodophenyl)pyridin-3-amine

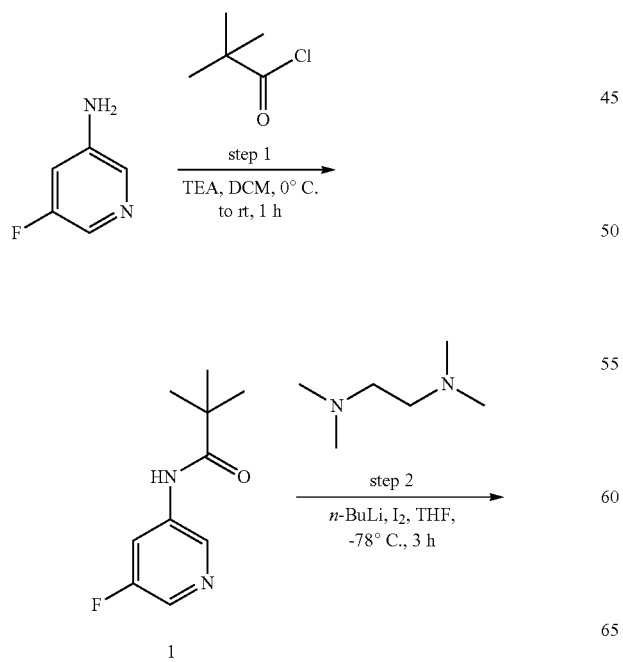

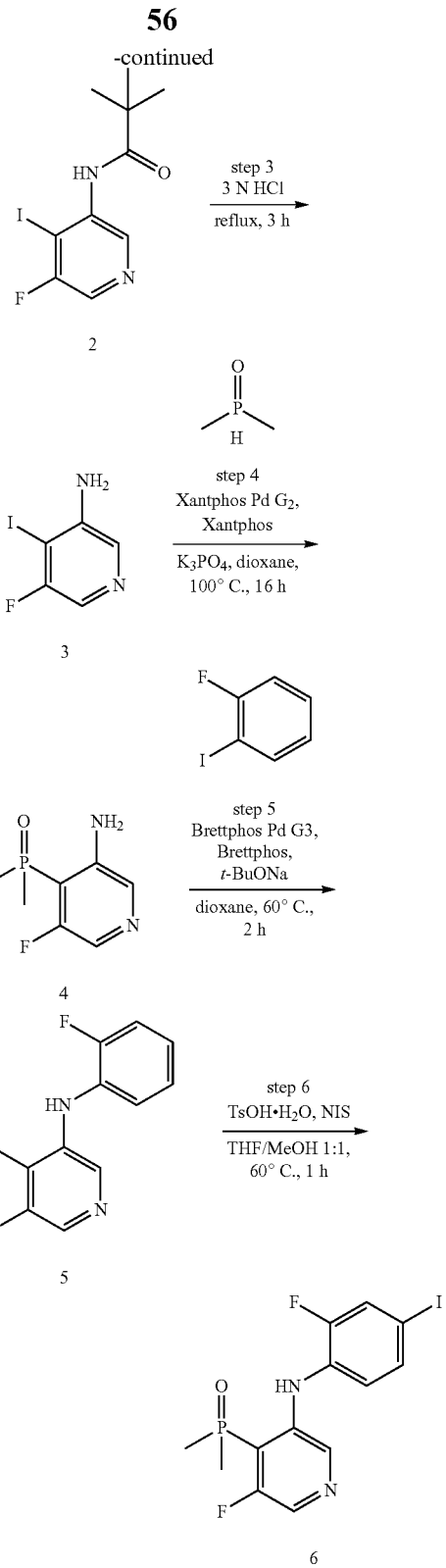

Step 1: N-(5-Fluoropyridin-3-yl)-2,2-dimethylpropanamide

To a stirred mixture of trifluoroacetic acid (27.08 g, 267.60 mmol) and 5-fluoropyridin-3-amine (10 g, 89.20 mmol) in dichlormethane (100 mL) was added 2,2-dimethylpropanoyl chloride (13.98 g, 115.96 mmol) dropwise at 0° C. The reaction mixture was stirred for 1 h at room temperature. The reaction was quenched by the addition of water (100 mL). The aqueous layer was extracted with dichlormethane (3×100 mL). The combined organic layers was washed with brine (3×100 mL), dried over anhydrous $Na_2SO_4$. After filtration, the filtrate was concentrated under reduced pressure to afford N-(5-fluoropyridin-3-yl)-2,2-dimethylpropanamide (9.35 g, crude) as a yellow solid. MS ESI calculated for $C_{10}H_{13}FN_2O$ [M+H]$^+$, 197.10 found 197.25; $^1$H NMR (400 MHz, CDCl$_3$) δ8.33-8.28 (m, 1H), 8.22-8.20 (m, 2H), 7.56 (s, 1H), 1.35 (s, 9H).

Step 2: N-(5-Fluoro-4-iodopyridin-3-yl)-2,2-dimethylpropanamide

To a stirred solution of N-(5-fluoropyridin-3-yl)-2,2-dimethylpropanamide (5.00 g, 25.48 mmol) and $N^1,N^1,N^2,N_2$-tetramethylethane-1,2-diamine (8.88 g, 76.44 mmol) in tetrahydrofuran (15 mL) was added n-Butyllithium (30.58 mL, 76.44 mmol, 2.5 M in hexanes) dropwise over 1 h at −78° C. under nitrogen atmosphere. The resulting mixture was stirred for 1 h at −78° C. under nitrogen atmosphere. To the above mixture was added iodine (19.40 g, 76.44 mmol) in THF (5 mL) dropwise over 30 min at −78° C. The resulting mixture was stirred for additional 1 h at −78° C. The reaction was quenched by the addition of Water (50 mL) at −78° C. The resulting mixture was decolorized by the addition of Sodium thiosulfate. The resulting mixture was extracted with ethyl acetate (3×100 mL). The combined organic layers was washed with brine (2×100 mL), dried over anhydrous sodium sulfate. After filtration, the filtrate was concentrated under reduced pressure. The residue was purified by silica gel column chromatography, eluted with Petroleum ether/Ethyl acetate (1/1). The fractions contained desired product were combined and concentrated to afford N-(5-fluoro-4-iodopyridin-3-yl)-2,2-dimethylpropanamide (4.7 g, 57%) as a white crystal. MS ESI calculated for $C_{10}H_{12}FN_2O$ [M+H]$^+$, 323.00, found 322.95; $^1$H NMR (400 MHz, CDCl$_3$) δ 9.24 (s, 1H), 8.13 (d, J=0.8 Hz, 1H), 7.75 (s, 1H), 1.42 (d, J=0.8 Hz, 9H).

Step 3: 5-Fluoro-4-iodopyridin-3-amine

A mixture of N-(5-fluoro-4-iodopyridin-3-yl)-2,2-dimethylpropanamide (4.7 g, 14.591 mmol, 1 equiv) in aqueous HCl (50 mL, 3 M) was stirred for 3 h at 100° C. The resulting mixture was basified with aqueous sodium hydroxide (50 mL, 3 M) at room temperature. The resulting mixture was extracted with dichloromethane (3×50 mL). The combined organic layers was washed with brine (1×50 mL), dried over anhydrous sodium sulfate. After filtration, the filtrate was concentrated under reduced pressure to afford 5-fluoro-4-iodopyridin-3-amine (3.5 g, crude) as a white solid. MS ESI calculated for $C_5H_4FIN$ [M+H]$^+$, 238.94, found 238.90; $^1$H NMR (400 MHz, CDCl$_3$) δ 7.85 (s, 1H), 7.74 (s, 1H), 4.35 (s, 2H).

Step 4: 4-(Dimethylphosphoryl)-5-fluoropyridin-3-amine

To a stirred mixture of 5-fluoro-4-iodopyridin-3-amine (200 mg, 0.84 mmol), 4,5-Bis(diphenylphosphino)-9,9-dimethylxanthene (48 mg, 0.08 mmol), Potassium phosphate tribasic (356 mg, 1.68 mmol,) and Chloro[9,9-dimethyl-4,5-bis(diphenylphosphino)xanthene][2-amino-1,1-biphenyl-2-yl]palladium (74 mg, 0.08 mmol) in 1,4-dioxane (5 mL) was added (methylphosphonoyl)methane (98 mg, 1.26 mmol). The reaction mixture was degassed with nitrogen for three times and stirred for 16 h at 100° C. The resulting mixture was concentrated under reduced pressure. The residue was purified by reverse phase Flash chromatography with the following conditions: Column: WelFlash™ C18-I, 20-40 μm, 120 g; Eluent A: Water (Plus 10 mmol/L formic acid); Eluent B: Acetonitrile; Gradient: 2%-15% B in 25 min; Flow rate: 60 mL/min; Detector: 220/254 nm. The fractions contained desired product were combined and concentrated to afford 4-(dimethylphosphoryl)-5-fluoropyridin-3-amine (130 mg, 82%) as a yellow oil. MS ESI calculated for $C_7H_{10}FN_2OP$ [M+H]$^+$, 189.05, found 189.05; $^1$H NMR (400 MHz, CDCl$_3$) δ 7.92 (s, 1H), 7.77 (s, 1H), 5.94 (s, 2H), 1.90-1.86 (m, 6H).

Step 5: 4-(Dimethylphosphoryl)-5-fluoro-N-(2-fluorophenyl)pyridin-3-amine

To a stirred mixture of 4-(dimethylphosphoryl)-5-fluoropyridin-3-amine (130 mg, 0.69 mmol), methanesulfonato2-dicyclohexylphosphino-3,6-dimethoxy-2'-4'-6'-tri-i-propyl-1,1'-bipheny)(2'-amino-1,1'-biphenyl-2-yl)palladium(II) (BrettPhos Pd G3) (62 mg, 0.06 mmol), 2-(dicyclohexylphosphino)-3,6-dimethoxy-2'-4'-6'-tri-i-propyl-1,1'-biphenyl (BrettPhos) (37 mg, 0.06 mmol) and sodium tert-butoxide (199 mg, 2.07 mmol) in 1,4-dioxane (2 mL) was added benzene, 1-fluoro-2-iodo- (153.40 mg, 0.69 mmol). The reaction mixture was degassed with nitrogen for three times and stirred for 1 h at 60° C. The resulting mixture was concentrated under reduced pressure. The residue was purified by reverse phase Flash chromatography with the following conditions: Column: WelFlash™ C18-I, 20-40 μm, 40 g; Eluent A: Water (Plus 10 mmol/L ammonium bicarbonate); Eluent B: acetonitrile; Gradient: 30/6-60% B in 25 min; Flow rate: 30 mL/min; Detector: 220/254 nm; desired fractions were collected at 50% B and concentrated under reduced pressure to afford 4-(dimethylphosphoryl)-5-fluoro-N-(2-fluorophenyl)pyridin-3-amine (100 mg, 51%) as a yellow solid. MS ESI calculated for $C_{13}H_{13}F_2N_2OP$ [M+H]$^+$, 283.07 found 282.95; $^1$H NMR (400 MHz, CDCl$_3$) δ 9.78 (s, 1H), 8.20-8.14 (m, 1H), 7.89 (d, J=4.4 Hz, 1H), 7.40-7.38 (m, 1H), 7.22-7.10 (m, 3H), 1.96 (dd, J=13.6, 1.8 Hz, 6H).

Step 6: 4-(Dimethylphosphoryl)-5-fluoro-N-(2-fluoro-4-iodophenyl)pyridin-3-amine To a stirred mixture of 4-(dimethylphosphoryl)-5-fluoro-N-(2-fluorophenyl)pyridin-3-amine (100 mg, 0.35 mmol) and N-iodosuccinimide (79 mg, 0.35 mmol) in tetrahydrofuran (0.5 mL) and methyl alcohol (0.5 mL) was added p-toluenesulfonic acid monohydrate (188 mg, 0.99 mmol). The reaction mixture was stirred for 1 h at 60° C. The resulting mixture was concentrated under reduced pressure. The residue was purified by reverse phase Flash chromatography with the following conditions: Column: WelFlash™ C18-I, 20-40 μm, 40 g; Eluent A: Water (Plus 10 mmol/L ammonium bicarbonate); Eluent B: acetonitrile; Gradient: 30%-60% B in 25 min; Flow rate: 30 mL/min; Detector: 220/254 nm. The fractions contained desired product were combined and concentrated to afford 4-(dimethylphosphoryl)-5-fluoro-N-(2-fluoro-4-iodophenyl)pyridin-3-amine (50 mg, 34%) as a white solid. MS ESI calculated for $C_{13}H_{12}F_2IN_2OP$ [M+H]$^+$, 408.97, found 408.95; $^1$H NMR (400 MHz, DMSO-d$_6$) δ 10.10 (s, 1H), 8.25 (d, J=3.6 Hz, 1H), 8.08 (d, J=4.4 Hz, 1H), 7.71 (dd, J=10.4, 2.0 Hz, 1H), 7.53 (d, J=8.8 Hz, 1H), 7.33 (t, J=8.4 Hz, 1H), 1.90 (dd, J=14.0, 1.8 Hz, 6H); ¹⁹F NMR (376 MHz, DMSO-d₆) −119.12 (1F), 123.01 (1F); ¹⁹P-NMR (162 MHz, DMSO-d₆) 43.20 (1P).

Example 25: (2-Fluoro-3-((2-fluoro-4-iodophenyl)amino)pyridin-4-yl)dimethylphosphine oxide

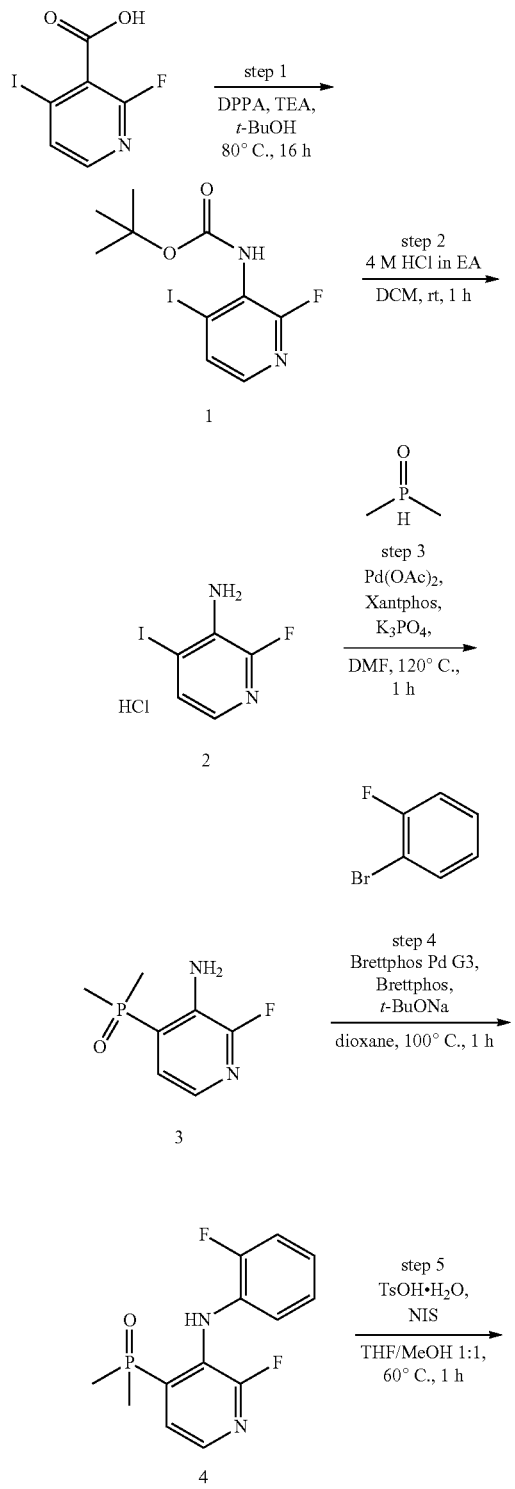

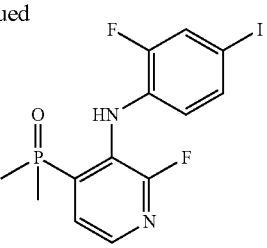

Step 1: Tert-butyl (2-fluoro-4-iodopyridin-3-yl)carbamate

To a stirred mixture of 2-fluoro-4-iodopyridine-3-carboxylic acid (3 g, 11.24 mmol) and DPPA (3.09 g, 11.24 mmol) in t-BuOH (30.00 mL) was added TEA (1.14 g 11.24 mmol) dropwise at room temperature under nitrogen atmosphere. The reaction mixture was stirred for 16 h at 80° C. under nitrogen atmosphere. The resulting mixture was concentrated under reduced pressure. The residue was purified by silica gel column chromatography, eluted with petroleum ether/ethyl acetate (5/1). The fractions contained desired product were combined and concentrated to afford tert-butyl (2-fluoro-4-iodopyridin-3-yl)carbamate (2.1 g, 55%) as a brown oil. MS ESI calculated for $C_{10}H_{12}FIN_2O_2[M+H]^+$, 338.99, found 338.95.

Step 2: 2-Fluoro-4-iodopyridin-3-amine hydrochloride

To a stirred solution of tert-butyl (2-fluoro-4-iodopyridin-3-yl)carbamate (2.1 g, 6.21 mmol) in DCM (10 mL) was added 4 M HCl (g) (20.99 mL, 83.97 mmol) dropwise at room temperature. The reaction mixture was stirred for 1 h at room temperature. The precipitated solids were collected by filtration and washed with DCM (3×30 mL). The crude product 2-fluoro-4-iodopyridin-3-amine hydrochloride (1.7 g, crude) was used in the next step directly without further purification. MS ESI calculated for $C_5H_5ClFIN_2$ [M+H−HCl]⁺, 238.94, found 239.05.

Step 3: (3-Amino-2-fluoropyridin-4-yl)dimethylphosphine oxide

To a stirred mixture of 2-fluoro-4-iodopyridin-3-amine hydrochloride (0.7 g, 2.94 mmol), (methylphosphonoyl)methane (0.28 g, 3.53 mmol), Pd(OAc)₂ (33.02 mg, 0.15 mmol) and XantPhos (85.09 mg, 0.15 mmol) in DMF (7.00 mL) was added K₃PO₄ (1.25 g, 5.88 mmol) in portions at room temperature. The reaction mixture was degassed with nitrogen for three times and stirred for 1 h at 120° C. The resulting mixture was concentrated under reduced pressure. The residue was purified by silica gel column chromatography, eluted with dichloromethane/methanol (10/1). The fractions contained desired product were combined and concentrated to afford 4-(dimethylphosphoryl)-2-fluoropyridin-3-amine (170 mg, 31%) as a brown solid. MS ESI calculated for $C_7H_{10}FN_2OP$ [M+H]⁺, 189.05, found 189.15.

Step 4: (2-Fluoro-3-((2-fluorophenyl)amino)pyridin-4-yl)dimethylphosphine oxide To a stirred mixture of 4-(dimethylphosphoryl)-2-fluoropyridin-3-amine (150 mg, 0.80 mmol), 2-(dicyclohexylphosphino)-3,6-dimethoxy-2'-4'-6'-tri-i-propyl-1,1'-biphenyl (BrettPhos) (42.80 mg, 0.08 mmol), t-BuONa (229.86 mg, 2.39 mmol) and methanesulfonato2-dicyclohexylphosphino-3,6-dimethoxy-2'-4'-6'-tri-i-propyl-1,1'-bipheny)(2'-amino-1,1'-biphenyl-2-yl)palladium(II) (BrettPhos Pd G3) (72.27 mg, 0.08 mmol) in dioxane (1.50 mL) was added 1-bromo-2-fluorobenzene (167.43 mg, 0.95 mmol) dropwise at room temperature. The reaction mixture was degassed with nitrogen for three times and stirred for 1 h at 100° C. The resulting mixture was concentrated under reduced pressure. The residue was purified by silica gel column chromatography, eluted with dichloromethane/methanol (10/1). The fractions contained desired product were combined and concentrated to afford (2-fluoro-3-((2-fluorophenyl)amino)pyridin-4-yl)dimethylphosphine oxide (130 mg, 58%) as a brown solid. MS ESI calculated for $C_{13}H_{13}FN_2OP$ $[M+H]^+$, 283.07, found 283.10.

Step 5: (2-Fluoro-3-((2-fluoro-4-iodophenyl)amino)pyridin-4-yl)dimethylphosphine oxide To a stirred mixture of (2-fluoro-3-((2-fluorophenyl)amino)pyridin-4-yl)dimethylphosphine oxide (110 mg, 0.39 mmol) and NIS (157.84 mg, 0.70 mmol) in THF (0.5 mL) and MeOH (0.5 mL) was added TsOH·H$_2$O (207.58 mg, 1.09 mmol) at room temperature under nitrogen atmosphere. The reaction mixture was stirred for 1 h at 60° C. under nitrogen atmosphere. The resulting mixture was concentrated under reduced pressure. The residue was purified by silica gel column chromatography, eluted with dichloromethane/methanol (10/1) to afford the crude product. The crude product was purified by Prep-HPLC with the following conditions: Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 32% B to 42% B in 8 min, 42% B; Wave Length: 254 nm; RTL: 7 min. The fractions contained desired product were combined and concentrated to afford (2-fluoro-3-((2-fluoro-4-iodophenyl)amino)pyridin-4-yl)dimethylphosphine oxide (34 mg, 21%) as an off-white solid. MS ESI calculated for $C_{13}H_{12}F_2IN_2OP$ $[M+H]^+$, 408.97, found 409.00; $^1$H NMR (400 MHz, DMSO-d$_6$) δ 8.84 (s, 1H), 8.06-8.02 (m, 1H), 7.64-7.55 (m, 2H), 7.39 (dd, J=8.0, 1.8 Hz, 1H), 6.61-6.56 (m, 1H), 1.79 (d, J=13.9 Hz, 6H); $^{19}$F NMR (376 MHz, DMSO-d$_6$) δ −71.75, −128.11; $^{31}$P NMR (162 MHz, DMSO-d$_6$) δ 41.15.

Example 30: 4-(Dimethylphosphoryl)-N-(2-fluoro-4-iodophenyl)-5-methylpyridin-3-amine

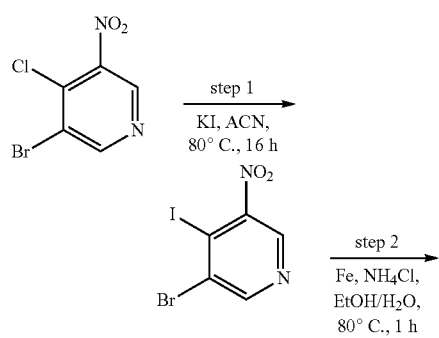

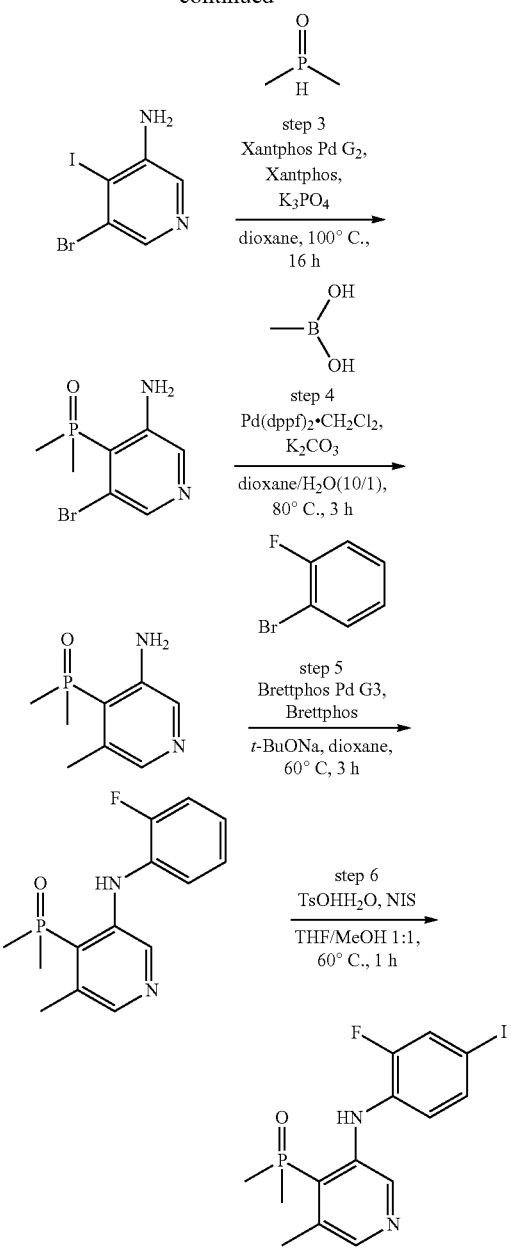

Step 1: 3-Bromo-4-iodo-5-nitropyridine

To a stirred solution of 3-bromo-4-chloro-5-nitropyridine (5 g, 21.06 mmol) and Potassium iodide (69.91 g, 421.16 mmol) in Acetonitrile (300 mL) was stirred for 16 h at 80° C. The resulting mixture was filtered, the filter cake was washed with acetonitrile (50 mL). The filtrate was concentrated under reduced pressure. The residue was purified by silica gel column chromatography, eluted with petroleum ether/ethyl acetate (10/1). The fractions contained desired product were combined and concentrated to afford 3-bromo-4-iodo-5-nitropyridine (6 g, 87%) as a yellow solid. MS ESI calculated for $C_5H_2BrIN_2O_2$ $[M+H]^+$, 328.83, 330.83, found 328.80, 330.80; $^1$H NMR (400 MHz, CDCl$_3$) δ 8.83 (s, 1H), 8.70 (s, 1H).

Step 2: 5-Bromo-4-iodopyridin-3-amine

To a stirred solution of 3-bromo-4-iodo-5-nitropyridine (2.4 g, 7.30 mmol) and Iron (1.63 g, 29.19 mmol) and ammonium chloride (1.95 g, 36.485 mmol) in ethanol (24 mL) and water (2.4 mL) at room temperature. The resulting mixture was stirred for 1 h at 80° C. The resulting mixture was filtered, the filter cake was washed with ethyl acetate (2×100 mL). The resulting mixture was extracted with ethyl acetate (1×100 mL). The combined organic layers was washed with brine (1×200 mL), dried over anhydrous sodium sulfate. After filtration, the filtrate was concentrated under reduced pressure. The residue was purified by silica gel column chromatography, eluted with petroleum ether/ethyl acetate (3/2). The fractions contained desired product were combined and concentrated to afford 5-bromo-4-iodopyridin-3-amine (2.5 g, 80%) as a yellow solid. MS ESI calculated for $C_5H_4BrIN_2$ [M+H]$^+$, 298.86, 300.86, found 298.80, 300.80; $^1$H NMR (400 MHz, CDCl$_3$) δ 8.04 (s, 1H), 7.88 (s, 1H), 4.37 (s, 2H).

Step 3: 5-Bromo-4-(dimethylphosphoryl)pyridin-3-amine

To a stirred solution of 5-bromo-4-iodopyridin-3-amine (2.2 g, 7.36 mmol) and (methylphosphonoyl)methane (861.69 mg, 11.04 mmol) and chloro[(4,5-bis(diphenylphosphino)-9,9-dimethylxanthene)-2-(2-amino-1,1-biphenyl)]palladium(II) (654.11 mg, 0.74 mmol) and 4,5-Bis(diphenylphosphino)-9,9-dimethylxanthene (425.88 mg, 0.74 mmol) in N,N-dimethylformamide (88 mL) was added potassium phosphate tribasic (3.12 g, 14.72 mmol) at room temperature. The reaction mixture was degassed with nitrogen for three times and stirred for 16 h at 100° C. The resulting mixture was concentrated under reduced pressure. The residue was purified by silica gel column chromatography, eluted with dichloromethane/methanol (12/1). The fractions contained desired product were combined and concentrated to afford 5-bromo-4-(dimethylphosphoryl)pyridin-3-amine (1 g, 54%) as a yellow solid. MS ESI calculated for $C_7H_{10}BrN_2OP$ [M+H]$^+$, 248.97, 250.97, found 248.90, 250.90; $^1$H NMR (400 MHz, CDCl$_3$) δ 7.95 (t, J=4.3 Hz, 2H), 6.23 (s, 2H), 2.04 (d, J=13.6 Hz, 6H).

Step 4: 4-(Dimethylphosphoryl)-5-methylpyridin-3-amine

To a stirred solution of 5-bromo-4-(dimethylphosphoryl)pyridin-3-amine (300 mg, 1.21 mmol) and methylboronic acid (72.11 mg, 1.21 mmol) and 1,1'-Bis(diphenylphosphino)ferrocene-palladium(II)dichloride dichloromethane complex (98.13 mg, 0.12 mmol) and potassium carbonate (499.44 mg, 3.62 mmol) in dioxane (3 mL) and water (0.3 mL) at room temperature. The reaction mixture was degassed with nitrogen for three times and stirred for 3 h at 80° C. The resulting mixture was concentrated under reduced pressure. The residue was purified by silica gel column chromatography, eluted with dichloromethane/methanol (9/1). The fractions contained desired product were combined and concentrated to afford 4-(dimethylphosphoryl)-5-methylpyridin-3-amine (240 mg, 92%) as a black semi-solid. MS ESI calculated for $C_8H_{13}N_2OP$ [M+H]$^+$, 185.08, found 185.05; $^1$H NMR (400 MHz, CDCl$_3$) δ 7.94 (s, 1H), 7.72 (s, 1H), 6.00 (s, 2H), 2.29 (s, 3H), 1.88 (d, J=13.2 Hz, 6H).

Step 5: 4-(Dimethylphosphoryl)-N-(2-fluorophenyl)-5-methylpyridin-3-amine

To a stirred solution of 4-(dimethylphosphoryl)-5-methylpyridin-3-amine (170 mg, 0.92 mmol) and 1-bromo-2-fluorobenzene (242.29 mg, 1.39 mmol) and methanesulfonato(2-dicyclohexylphosphino-3,6-dimethoxy-2',4',6'-tri-i-propyl-1,1'-biphenyl)(2'-amino-1,1'-biphenyl-2-yl)palladium(II) (83.67 mg, 0.09 mmol) and 2-(Dicyclohexylphosphino)-3,6-dimethoxy-2'-4'-6'-tri-i-propyl-1,1'-biphenyl (99.09 mg, 0.19 mmol) in dioxane (1.70 mL) was added sodium tert-butoxide (266.12 mg, 2.77 mmol) at room temperature. The reaction mixture was degassed with nitrogen for three times and stirred for 3 h at 60° C. The resulting mixture was concentrated under reduced pressure. The residue was purified by silica gel column chromatography, eluted with dichloromethane/methanol (12/1). The fractions contained desired product were combined and concentrated to afford 4-(dimethylphosphoryl)-N-(2-fluorophenyl)-5-methylpyridin-3-amine (250 mg, 97%) as a yellow solid. MS ESI calculated for $C_{14}H_{16}FN_2OP$ [M+H]+, 279.10, found 279.05; $^1$H NMR (400 MHz, CDCl$_3$) δ 10.03 (s, 1H), 8.27 (d, J=3.2, 1H), 7.86 (d, J=4.8 Hz, 1H), 7.36-7.35 (m, 1H), 7.17-6.98 (m, 3H), 2.36 (s, 3H), 1.95 (d, J=13.2 Hz, 6H).

Step 6: 4-(Dimethylphosphoryl)-N-(2-fluoro-4-iodophenyl)-5-methylpyridin-3-amine To a stirred solution of 4-(dimethylphosphoryl)-N-(2-fluorophenyl)-5-methylpyridin-3-amine (220 mg, 0.79 mmol) and N-Iodosuccinimide (533.62 mg, 2.37 mmol) in tetrahydrofuran (2.20 mL) and methanol (2.20 mL) was added p-toluenesulfonic acid·H$_2$O (421.07 mg, 2.22 mmol). The reaction mixture was stirred for 1 h at 60° C. The resulting mixture was concentrated under reduced pressure. The residue was purified by silica gel column chromatography, eluted with dichloromethane/methanol (9/1) to afford the crude product. The crude product was purified by Prep-HPLC with the following conditions Column: XBridge Shield RP18 OBD Column, 30×150 mm, 5 μm; Mobile Phase A: Water (Plus 10 mmol/L NH$_4$HCO$_3$), Mobile Phase B: ACN; Flow rate: 60 mL/min; Gradient: 30% B to 42% B in 8 min, 42% B; Wave Length: 254 nm. The fractions contained desired product were combined and concentrated to afford 4-(dimethylphosphoryl)-N-(2-fluoro-4-iodophenyl)-5-methylpyridin-3-amine (53.8 mg, 17%) as an off-white solid. MS ESI calculated for $C_{14}H_{15}FIN_2OP$ [M+H]$^+$, 405.00, found 415.15; $^1$H NMR (400 MHz, DMSO-d$_6$) δ 10.23 (s, 1H), 8.26 (d, J=4.8 Hz, 1H), 7.98 (d, J=4.8 Hz, 1H), 7.64 (dd, J=10.5, 1.9 Hz, 1H), 7.45 (d, J=9.2, 1H), 7.15 (t, J=8.8 Hz, 1H), 2.38 (s, 3H), 1.89 (d, J=13.6 Hz, 6H).

II. Biological Evaluation

Example 1: Cellular Assay

To determine the effect of the MEK inhibitor compounds disclosed herein on cellular MAPK signaling downstream of MEK, an assay monitoring phosphorylation of ERK was used. Melanoma derived cell line A-375, which harbors a BRAF V600 activating mutation was cultured and maintained as specified by the supplier (ATCC: Cat #CRL-1619; American Type Culture Collection; Manassas, Va. 20110). Cells were seeded at 8000 cells/well in 24 μL growth media in a 384-well plate and allowed to adhere at 37° C. with 5% CO$_2$ overnight. The following day, compounds were serially diluted into 10-point, 3-fold dilution curves in 384 well plates. Compound was transferred to cell plates using Echo550 such that the final concentration range was 0.508 nM to 10 mM in 0.1% DMSO with 0.1% DMSO being used as negative control. Cells were incubated with compounds for 1 hour at 37° C. with 5% $CO_2$. Cells were lysed by addition of 8 μL 4× lysis buffer provided with HTRF kit (Advanced phospho-ERK (Thr202/Tyr204) cellular kit; Cisbio; Cat #64AERPEH) plus 1× protease/phosphatase inhibitor cocktail. 20 μL lysate was transferred to HTRF plate followed by 2.5 μL each of anti-ERK1/2-Europium/Terbium Cryptate and anti-phospho-ERK1/2 antibody solutions per manufacturer's instructions and incubated. Specific signal was measured at 665 nm (donor) and 620 nm (acceptor) on a Perkin Elmer Envision 2105 and the ratios used to calculate $IC_{50}$ values within the Dotmatics Knowledge Solutions Studies curve fitting environment (Dotmatics, Bishops Stortford, MK CM23) and are presented in Table 8.

TABLE 8

| Synthetic Chemistry Example | A375 pERK $IC_{50}$ |
|---|---|
| 1 | A |
| 2 | D |
| 3 | B |
| 4 | D |
| 5 | B |
| 6 | B |
| 7 | B |
| 8 | B |
| 9 | B |
| 10 | C |
| 11 | C |
| 12 | C |
| 13 | A |
| 14 | B |
| 15 | C |
| 16 | C |
| 17 | C |
| 18 | C |
| 19 | C |
| 20 | C |
| 21 | C |
| 22 | B |
| 23 | B |
| 24 | A |
| 25 | B |
| 26 | A |
| 27 | C |
| 28 | C |
| 29 | B |
| 30 | A |
| 31 | B |
| 32 | B |

A: >0.010 μM
B: >0.01 μM to ≤0.10 μM
C: >0.10 μM to ≤1 μM
D: ≤1 μM

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg–eq/mL.

The examples and embodiments described herein are for illustrative purposes only and various modifications or changes suggested to persons skilled in the art are to be included within the spirit and purview of this application and scope of the appended claims.

We claim:
1. A compound, or pharmaceutically acceptable salt or solvate thereof, having the structure of Formula (I):

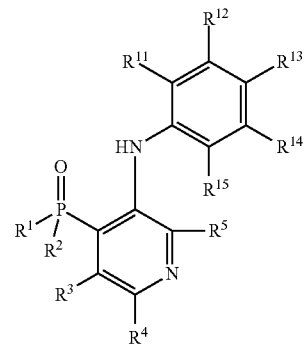

wherein,
$R^1$ is optionally substituted alkyl;
$R^2$ is optionally substituted alkyl; or $R^1$ and $R^2$ join with a carbon-carbon bond to form a phosphorous-containing ring;
$R^3$ is selected from hydrogen, halo, optionally substituted alkyl, optionally substituted cycloalkyl, or optionally substituted alkoxy;
$R^4$ is selected from hydrogen, halo, optionally substituted alkyl, optionally substituted cycloalkyl, or optionally substituted alkoxy;
$R^5$ is selected from hydrogen, halo, optionally substituted alkyl, optionally substituted cycloalkyl, or optionally substituted alkoxy; and
$R^{11}$, $R^{12}$, $R^{13}$, $R^{14}$, and $R^{15}$ are independently selected from hydrogen, halo, optionally substituted alkynyl, optionally substituted alkyl, or optionally substituted cycloalkyl.

2. The compound of claim 1, or pharmaceutically acceptable salt or solvate thereof, wherein $R^1$ is optionally substituted C1-C3 alkyl.

3. The compound of claim 1, or pharmaceutically acceptable salt or solvate thereof, wherein $R^2$ is optionally substituted C1-C3 alkyl.

4. The compound of claim 1, or pharmaceutically acceptable salt or solvate thereof, wherein $R^1$ is $CH_3$.

5. The compound of claim 1, or pharmaceutically acceptable salt or solvate thereof, wherein $R^2$ is $CH_3$.

6. The compound of claim 1, or pharmaceutically acceptable salt or solvate thereof, wherein $R^3$ is hydrogen.

7. The compound of claim 1, or pharmaceutically acceptable salt or solvate thereof, wherein $R^3$ is halo.

8. The compound of claim 1, or pharmaceutically acceptable salt or solvate thereof, wherein $R^3$ is optionally substituted C1-C3 alkyl.

9. The compound of claim 1, or pharmaceutically acceptable salt or solvate thereof, wherein $R^4$ is hydrogen.

10. The compound of claim 1, or pharmaceutically acceptable salt or solvate thereof, wherein $R^4$ is halo.

11. The compound of claim 1, or pharmaceutically acceptable salt or solvate thereof, wherein $R^4$ is optionally substituted C1-C3 alkyl.

12. The compound of claim 1, or pharmaceutically acceptable salt or solvate thereof, wherein $R^4$ is optionally substituted C1-C3 alkoxy.

13. The compound of claim 1, or pharmaceutically acceptable salt or solvate thereof, wherein $R^5$ is hydrogen.

14. The compound claim 1, or pharmaceutically acceptable salt or solvate thereof, wherein $R^5$ is halo.

15. The compound of claim 1, or pharmaceutically acceptable salt or solvate thereof, wherein $R^5$ is optionally substituted C1-C3 alkyl.

16. The compound of claim 1, or pharmaceutically acceptable salt or solvate thereof, wherein $R^5$ is optionally substituted C1-C3 alkoxy.

17. The compound of claim 1, or pharmaceutically acceptable salt or solvate thereof, wherein $R^{11}$ is fluoro.

18. The compound of claim 1, or pharmaceutically acceptable salt or solvate thereof, wherein $R^{11}$ is hydrogen.

19. The compound of claim 1, or pharmaceutically acceptable salt or solvate thereof, wherein $R^{12}$ is hydrogen or fluoro.

20. The compound of claim 1, or pharmaceutically acceptable salt or solvate thereof, wherein $R^{13}$ is selected from iodo, bromo, optionally substituted C2-C3 alkynyl, optionally substituted C1-C3 alkyl, or optionally substituted C3-C4 cycloalkyl.

21. The compound of claim 1, or pharmaceutically acceptable salt or solvate thereof, wherein $R^{13}$ is iodo.

22. The compound of claim 1, or pharmaceutically acceptable salt or solvate thereof, wherein $R^{13}$ is optionally substituted C1 alkyl.

23. The compound of claim 1, or pharmaceutically acceptable salt or solvate thereof, wherein $R^{13}$ is —$CF_3$.

24. The compound of claim 1, or pharmaceutically acceptable salt or solvate thereof, wherein $R^{13}$ is bromo.

25. The compound of claim 1, or pharmaceutically acceptable salt or solvate thereof, wherein $R^{13}$ is optionally substituted cyclopropyl.

26. The compound of claim 1, or pharmaceutically acceptable salt or solvate thereof, wherein $R^{14}$ and $R^{15}$ are hydrogen.

27. A pharmaceutical composition comprising a compound, or pharmaceutically acceptable salt or solvate thereof, as described in claim 1 and a pharmaceutically acceptable excipient.

* * * * *